(12) United States Patent
Aftanas et al.

(10) Patent No.: US 7,448,523 B2
(45) Date of Patent: Nov. 11, 2008

(54) VEHICLE ARTICLE CARRIER HAVING STOWABLE CROSS BARS

(75) Inventors: Jeffrey M Aftanas, Ortonville, MI (US); Gerard J Kmita, Allen Park, MI (US); Donald R Potter, Clarkston, MI (US)

(73) Assignee: JAC Products, Inc., Saline, MI (US)

( * ) Notice: Subject to any disclaimer, the term of this patent is extended or adjusted under 35 U.S.C. 154(b) by 765 days.

(21) Appl. No.: 10/925,660

(22) Filed: Aug. 25, 2004

(65) Prior Publication Data

US 2005/0199666 A1  Sep. 15, 2005

Related U.S. Application Data

(60) Division of application No. 10/850,595, filed on May 19, 2004, now Pat. No. 7,090,103, which is a continuation-in-part of application No. 10/700,335, filed on Nov. 3, 2003, now Pat. No. 7,066,364, which is a continuation-in-part of application No. 10/700,334, filed on Nov. 3, 2003, now Pat. No. 6,959,845, which is a continuation-in-part of application No. 10/279,295, filed on Oct. 24, 2002, now Pat. No. 6,751,992.

(51) Int. Cl.
  *B60R 9/00* (2006.01)
(52) U.S. Cl. .................... 224/321; 224/325; 224/326; 280/769
(58) Field of Classification Search ........... 224/321, 224/322, 324, 325, 326, 549, 553, 554, 924; 280/762, 769; 414/462
See application file for complete search history.

(56) References Cited

U.S. PATENT DOCUMENTS

| | | | |
|---|---|---|---|
| 3,670,935 A | 6/1972 | Hinkston | |
| 3,838,802 A | 10/1974 | Grycel, III | |
| 4,132,335 A | 1/1979 | Ingram | |
| 4,225,068 A | 9/1980 | Ingram | |
| 4,239,138 A | 12/1980 | Kowalski | |
| 4,295,587 A | 10/1981 | Bott | |
| 4,345,705 A | 8/1982 | Graber | |
| 4,406,386 A | 9/1983 | Rasor et al. | |

(Continued)

FOREIGN PATENT DOCUMENTS

DE  2939672  4/1981

(Continued)

*Primary Examiner*—Gary E Elkins
(74) *Attorney, Agent, or Firm*—Harness, Dickey & Pierce, P.L.C.

(57) ABSTRACT

A vehicle article carrier having a pair of cross bars that can be positioned in a stowed, position, resting on or adjacent to a corresponding pair of siderails, or moved into an operative position with the cross bars extending perpendicularly between the siderails. The cross bars are completely removable from each of the side rails. When the cross bars are in the stowed position, the apparatus presents a significantly more aerodynamic structure that helps to reduce wind noise when the vehicle on which the apparatus is mounted is being driven. The cross bars can be quickly moved into the operative position via latching mechanisms disposed at end that can be released from a securing structure at a forward portion and a rearward portion of each siderail and re-attached to a securing portion of the other siderail.

20 Claims, 27 Drawing Sheets

U.S. PATENT DOCUMENTS

| | | | |
|---|---|---|---|
| 4,416,406 A | 11/1983 | Popeney | |
| 4,469,261 A | 9/1984 | Stapleton et al. | |
| 4,473,178 A | 9/1984 | Bott | |
| 4,487,348 A | 12/1984 | Mareydt | |
| 5,004,139 A | 4/1991 | Storm et al. | |
| 5,071,050 A | 12/1991 | Pudney et al. | |
| 5,104,018 A | 4/1992 | Dixon | |
| 5,273,195 A | 12/1993 | Cucheran et al. | |
| 5,340,007 A | 8/1994 | Jeuffray et al. | |
| 5,372,287 A | 12/1994 | Deguevara | |
| 5,377,890 A | 1/1995 | Brunner et al. | |
| 5,385,285 A | 1/1995 | Cucheran et al. | |
| 5,395,024 A | 3/1995 | Luchtenberg | |
| 5,411,196 A | 5/1995 | Lee, Jr. et al. | |
| 5,464,140 A | 11/1995 | Hill | |
| 5,470,003 A | 11/1995 | Cucheran | |
| 5,511,709 A | 4/1996 | Fisch | |
| 5,529,231 A | 6/1996 | Burgess | |
| 5,549,229 A | 8/1996 | Grabowski | |
| 5,577,649 A | 11/1996 | Lee et al. | |
| 5,588,572 A | 12/1996 | Cronce et al. | |
| 5,624,063 A | 4/1997 | Ireland | |
| 5,758,810 A | 6/1998 | Stapleton | |
| 5,782,391 A | 7/1998 | Cretcher | |
| 5,791,536 A | 8/1998 | Stapleton | |
| 5,826,766 A | 10/1998 | Aftanas | |
| 5,845,829 A | 12/1998 | Stapleton | |
| 5,884,824 A | 3/1999 | Spring, Jr. | |
| 6,015,074 A | 1/2000 | Snavely et al. | |
| 6,102,265 A | 8/2000 | Stapleton | |
| 6,286,739 B1 | 9/2001 | Stapleton | |
| 6,409,063 B1 | 6/2002 | Kmita et al. | |
| 6,415,970 B1 | 7/2002 | Kmita et al. | |
| 6,722,541 B1 | 4/2004 | Aftanas et al. | |
| 6,811,066 B2 | 11/2004 | Aftanas et al. | |
| 6,959,845 B2 | 11/2005 | Aftanas et al. | |
| 7,066,364 B2 * | 6/2006 | Kmita et al. | 224/321 |
| 7,090,103 B2 * | 8/2006 | Aftanas et al. | 224/321 |

FOREIGN PATENT DOCUMENTS

| | | |
|---|---|---|
| DE | 2945950 | 5/1981 |
| DE | 3029586 | 3/1982 |
| DE | 3201409 | 9/1983 |
| DE | 3641745 | 6/1988 |
| DE | 3814799 | 11/1988 |
| EP | 1 470 960 | 10/2004 |
| FR | 2661378 | 10/1991 |
| FR | 2699475 | 6/1994 |
| FR | 2713568 | 6/1995 |
| GB | 2 381 252 | 4/2003 |
| JP | 5-502199 | 4/1993 |
| JP | 11-034751 | 2/1999 |
| WO | WO 9108929 | 6/1991 |

* cited by examiner

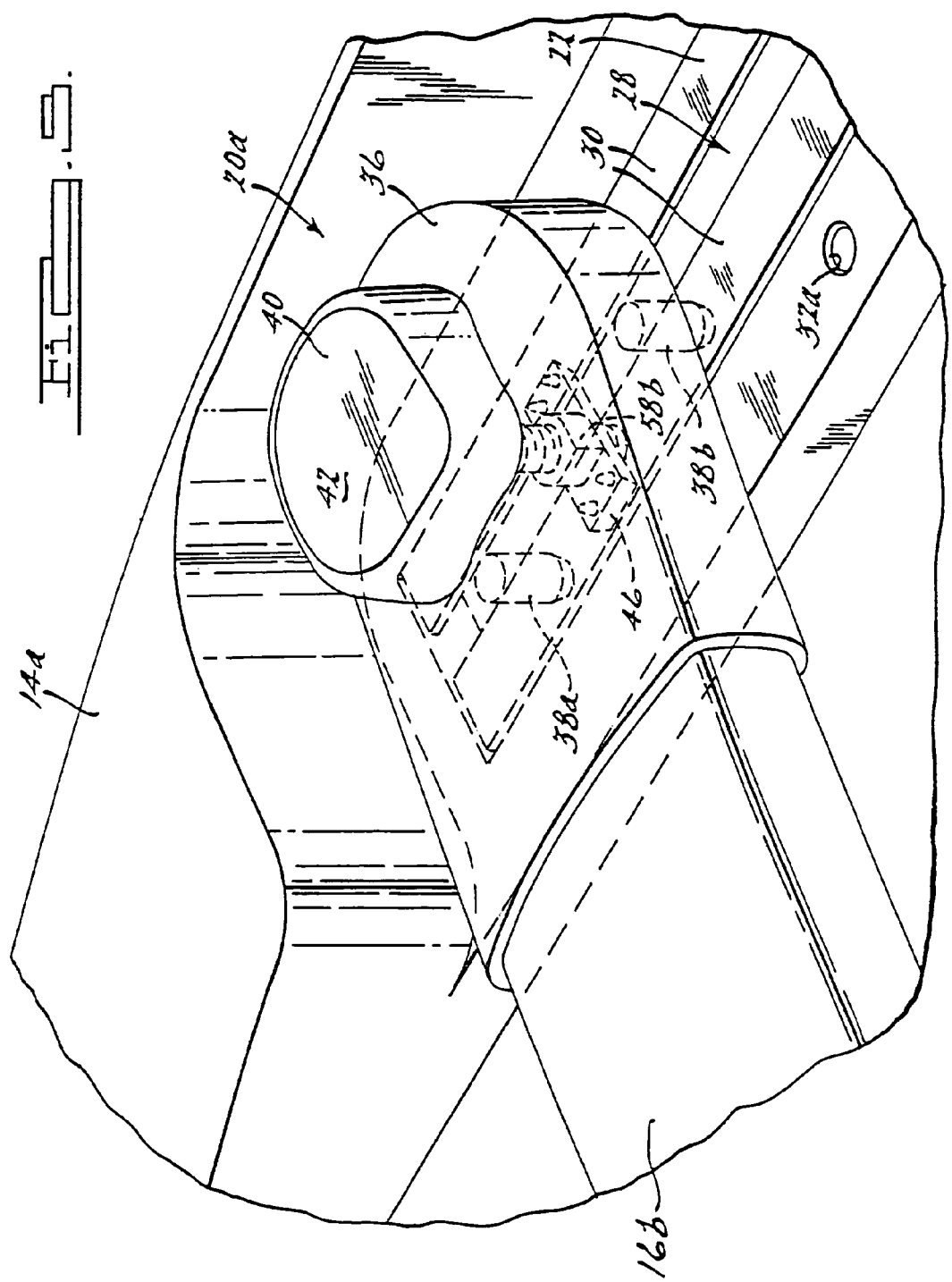

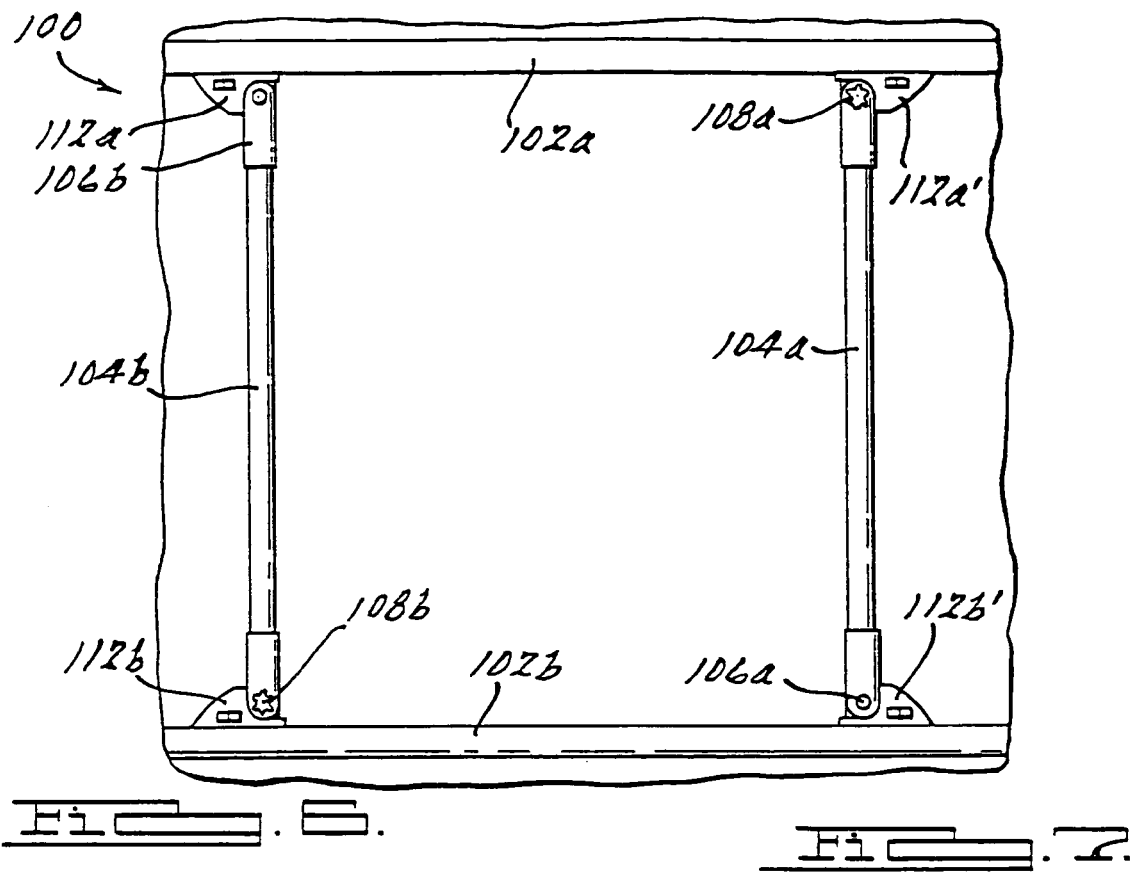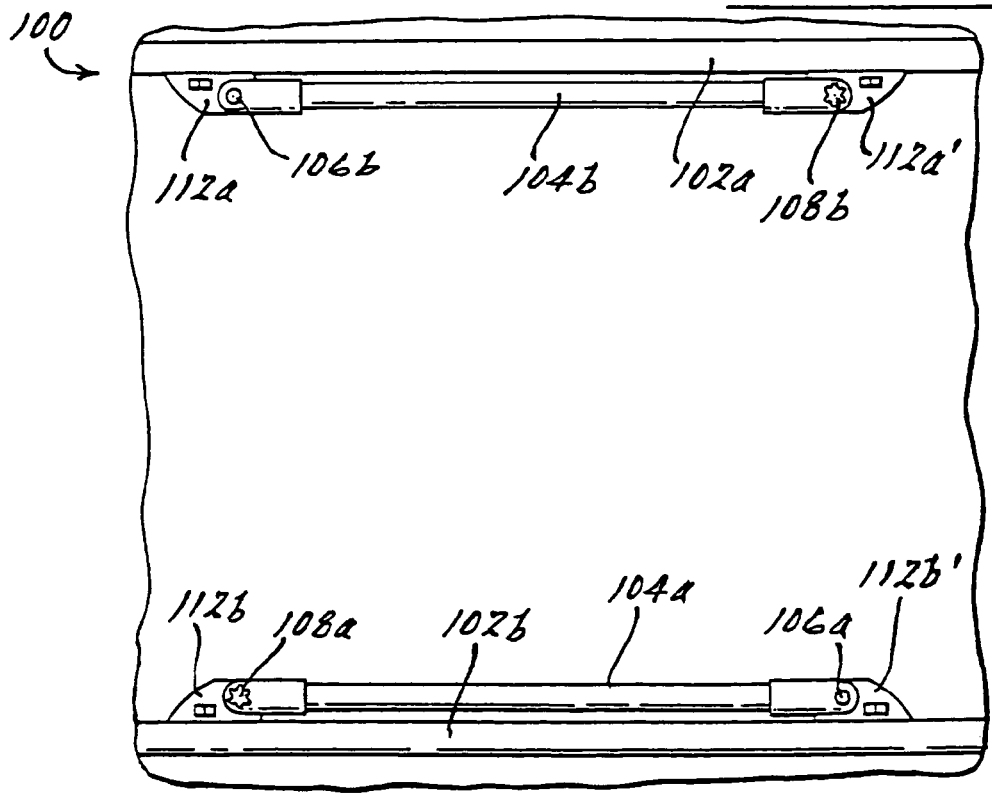

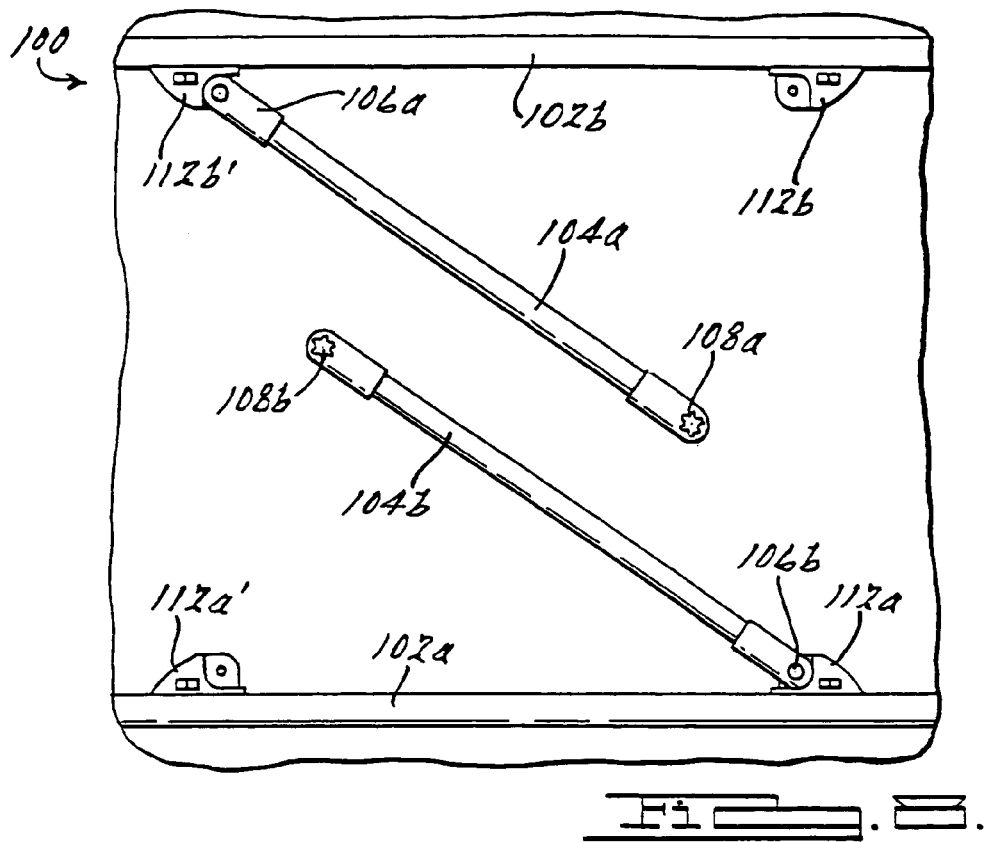
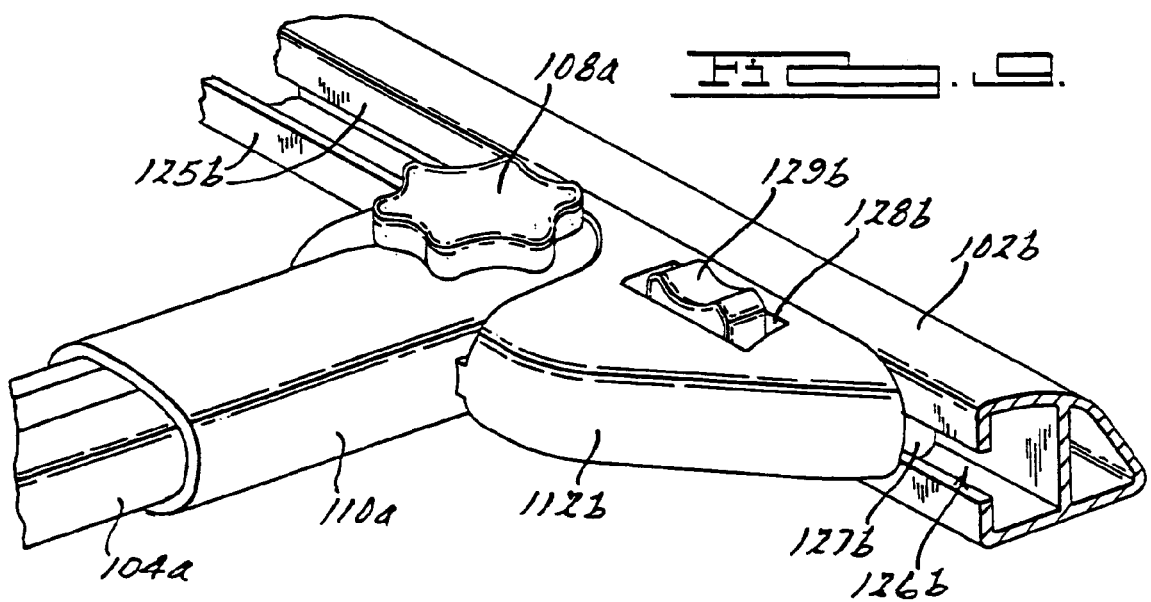

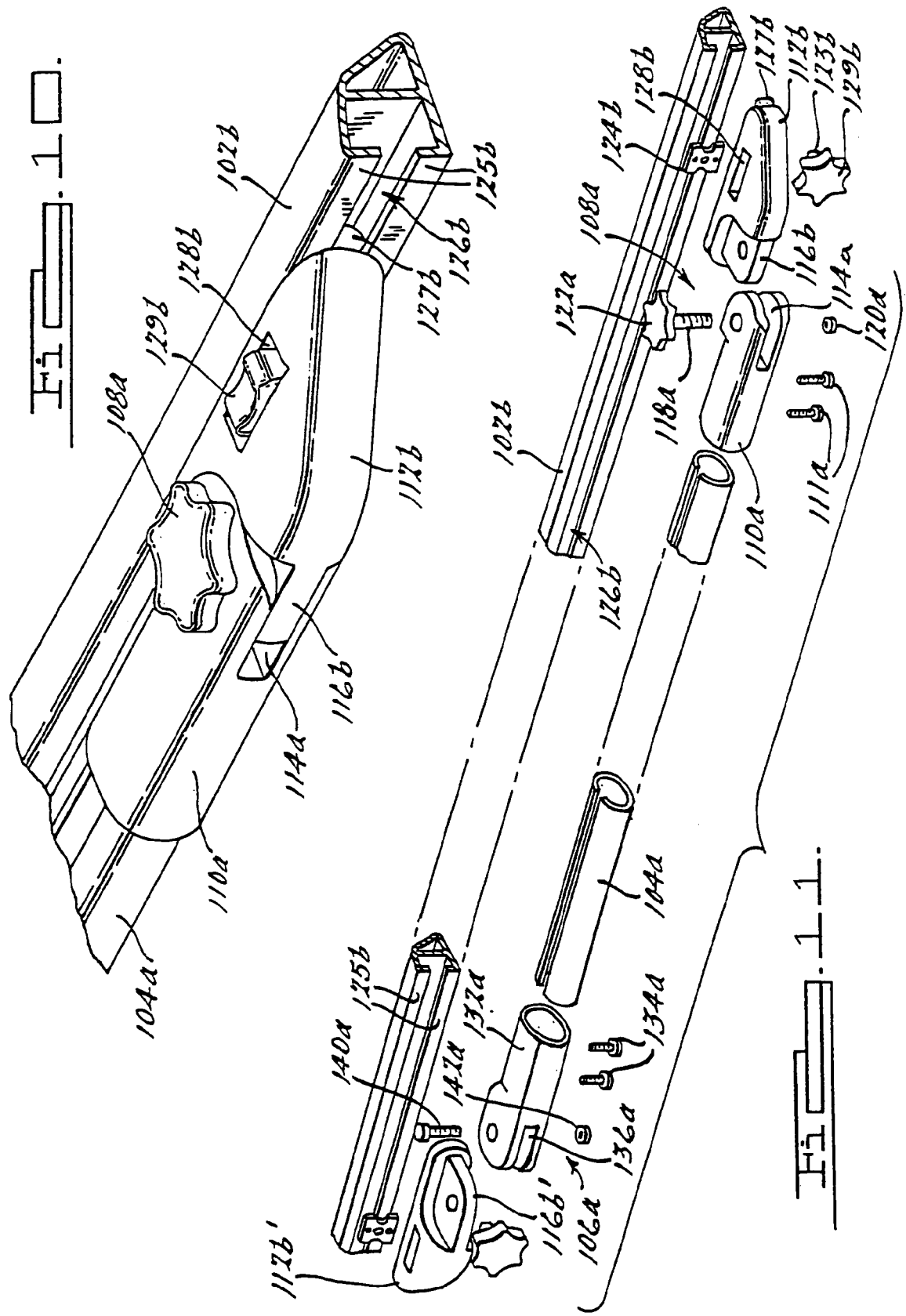

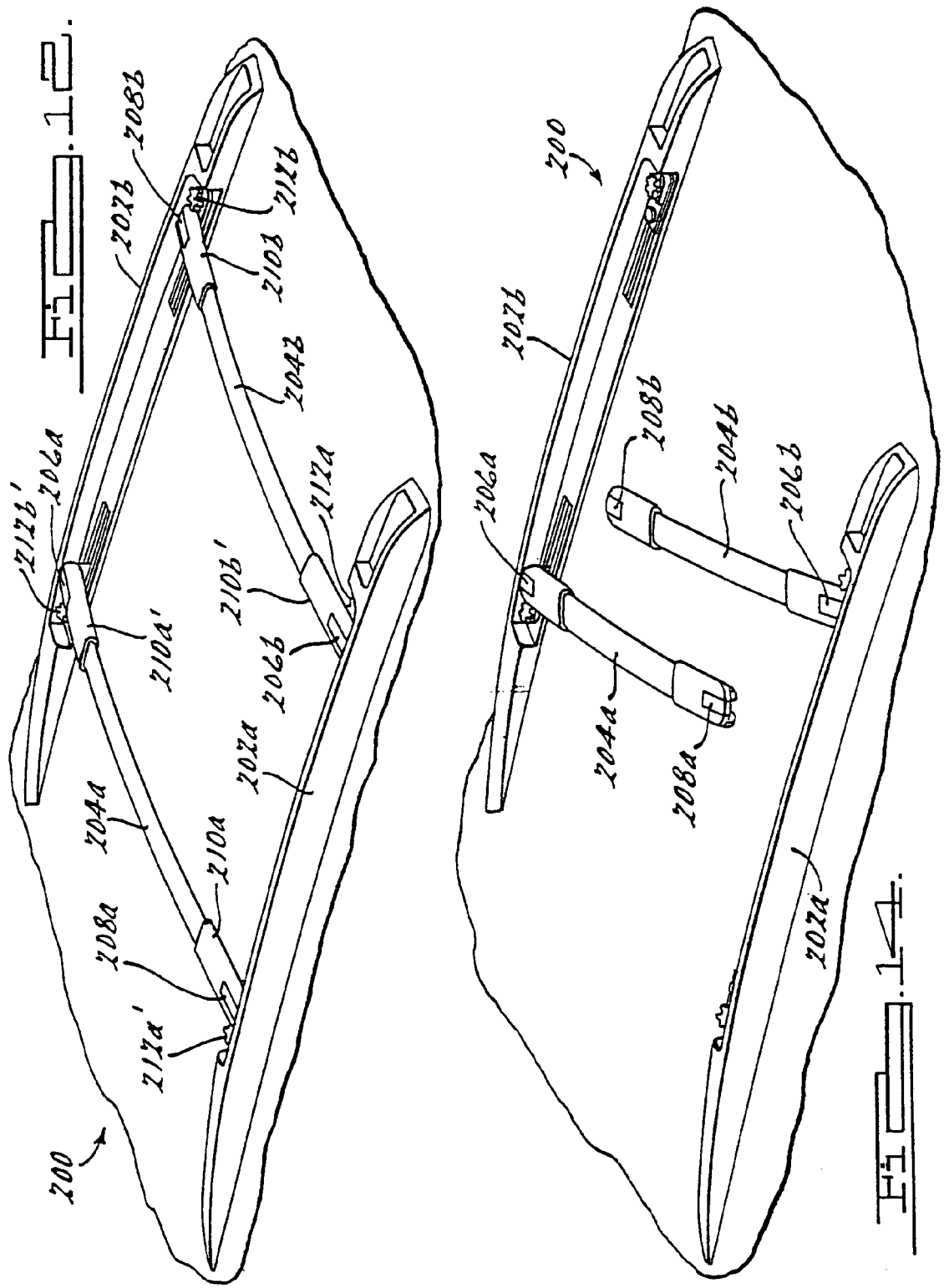

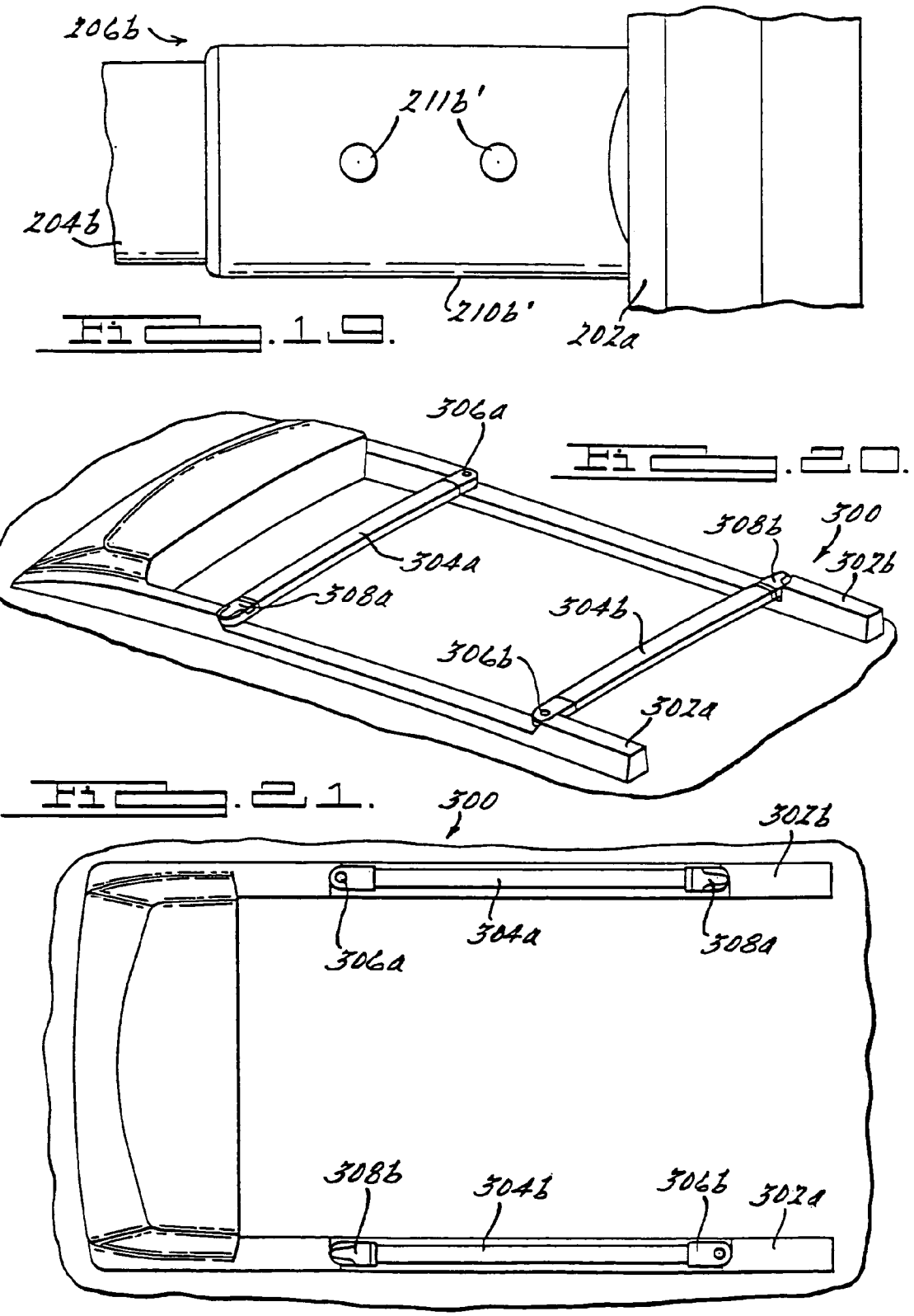

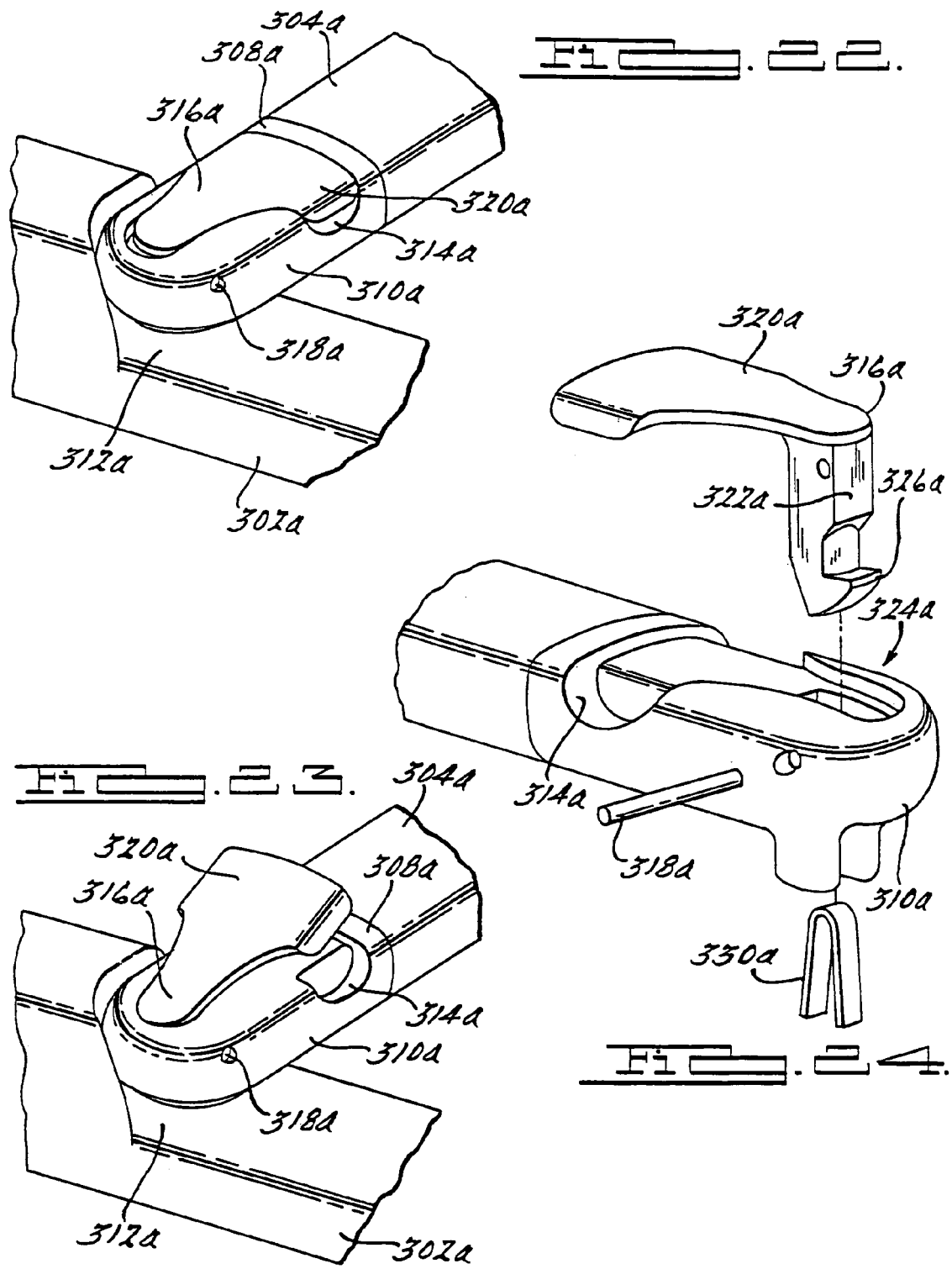

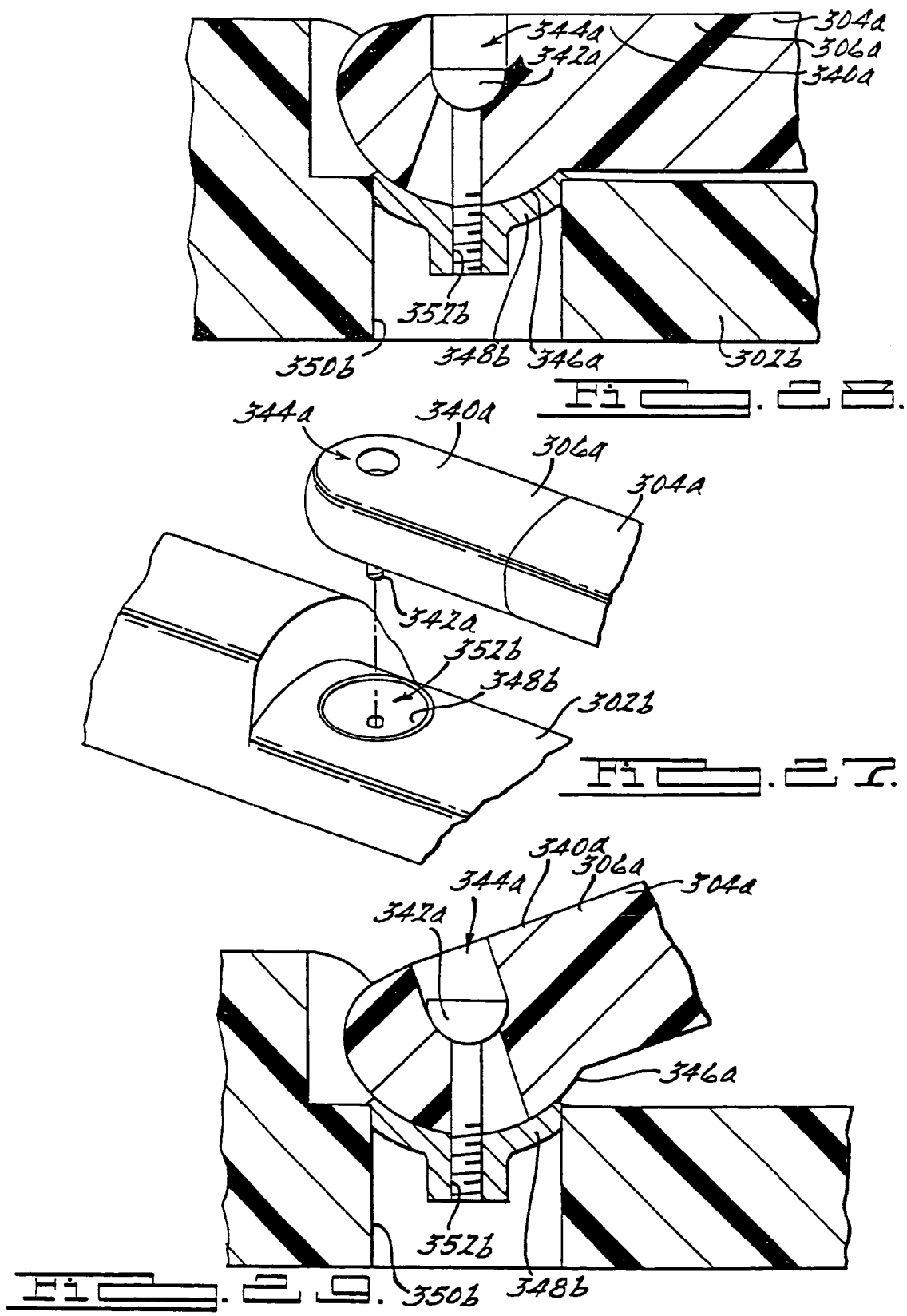

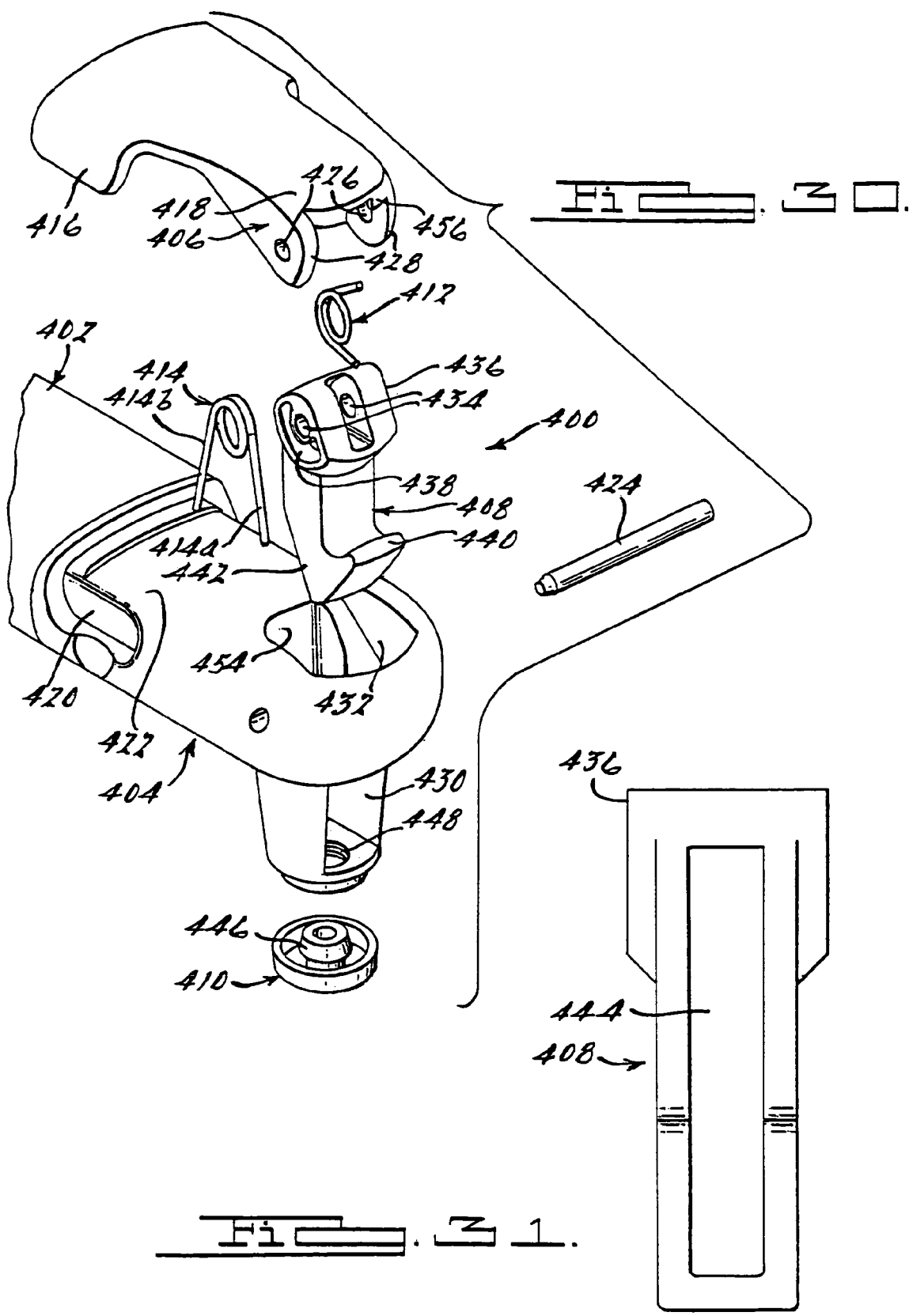

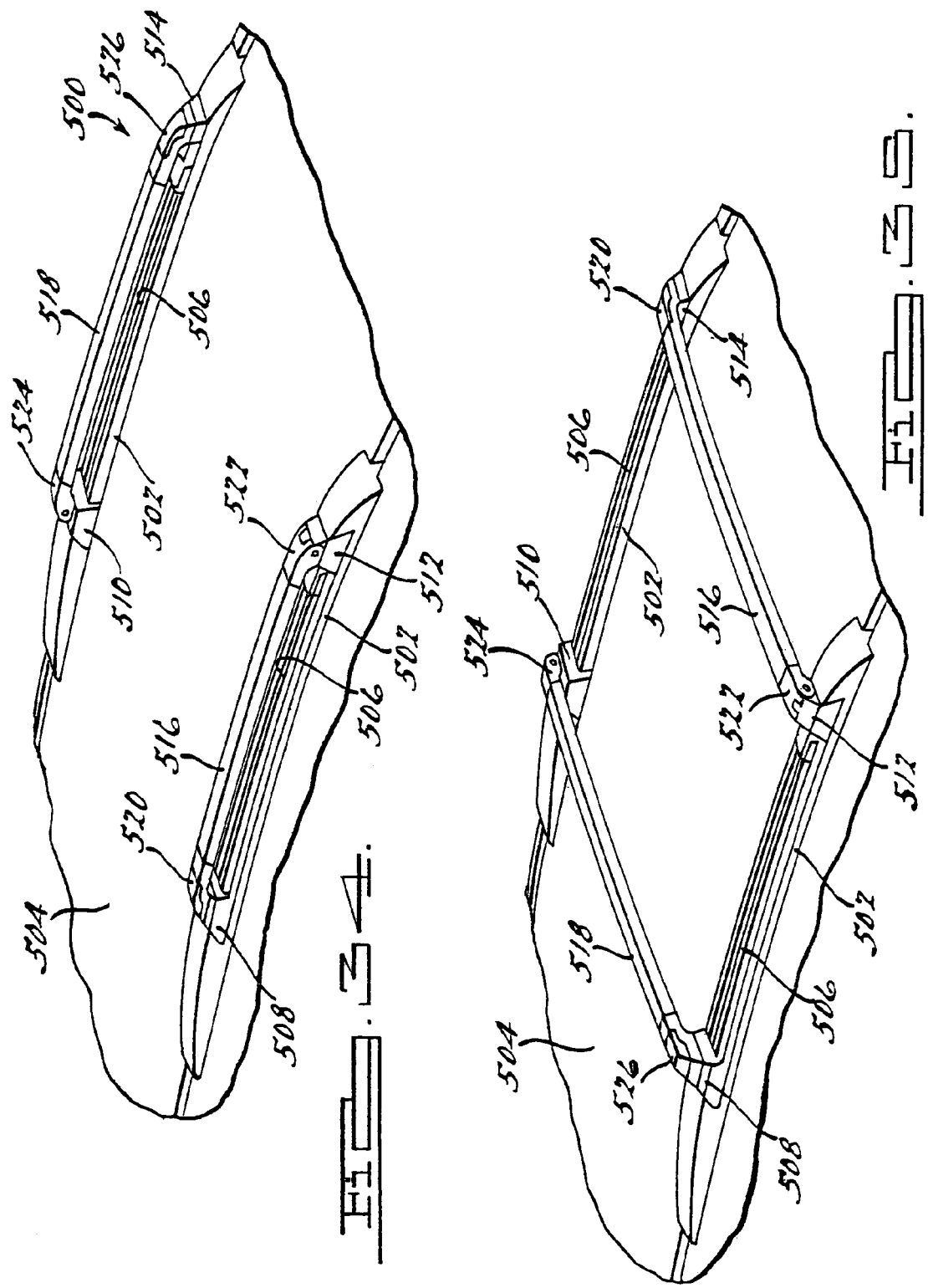

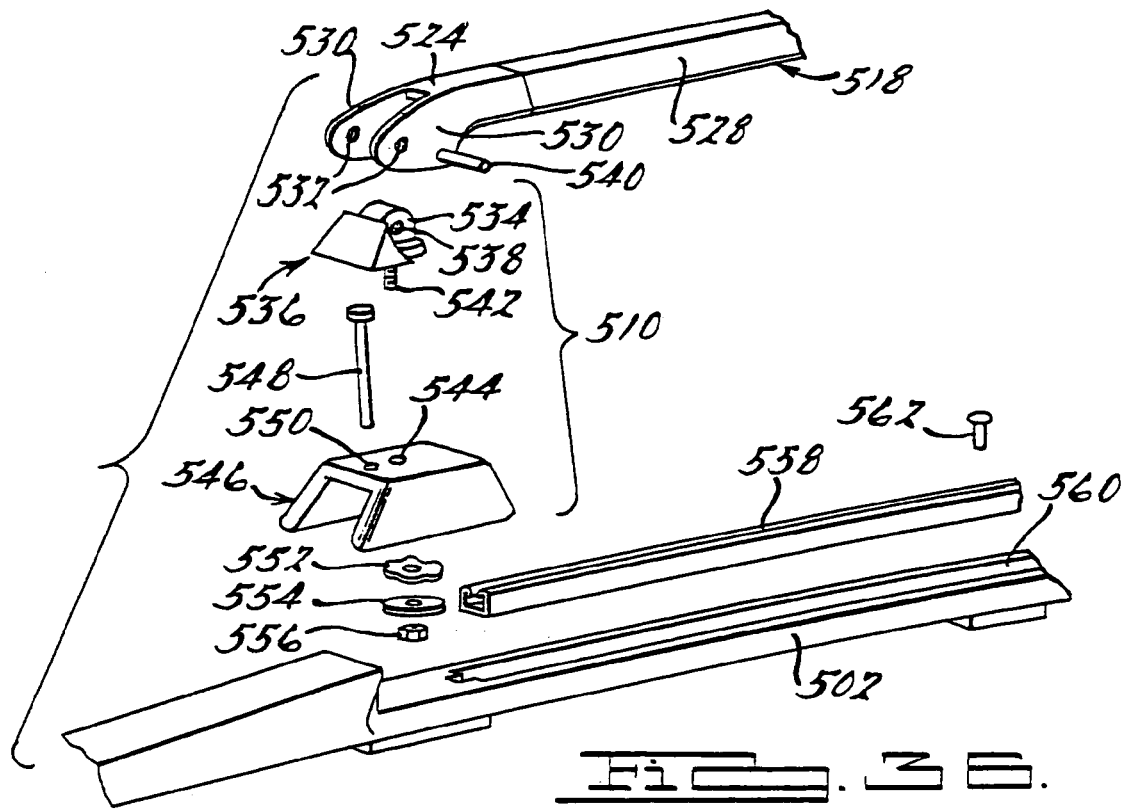
FIG. 36.
FIG. 37.
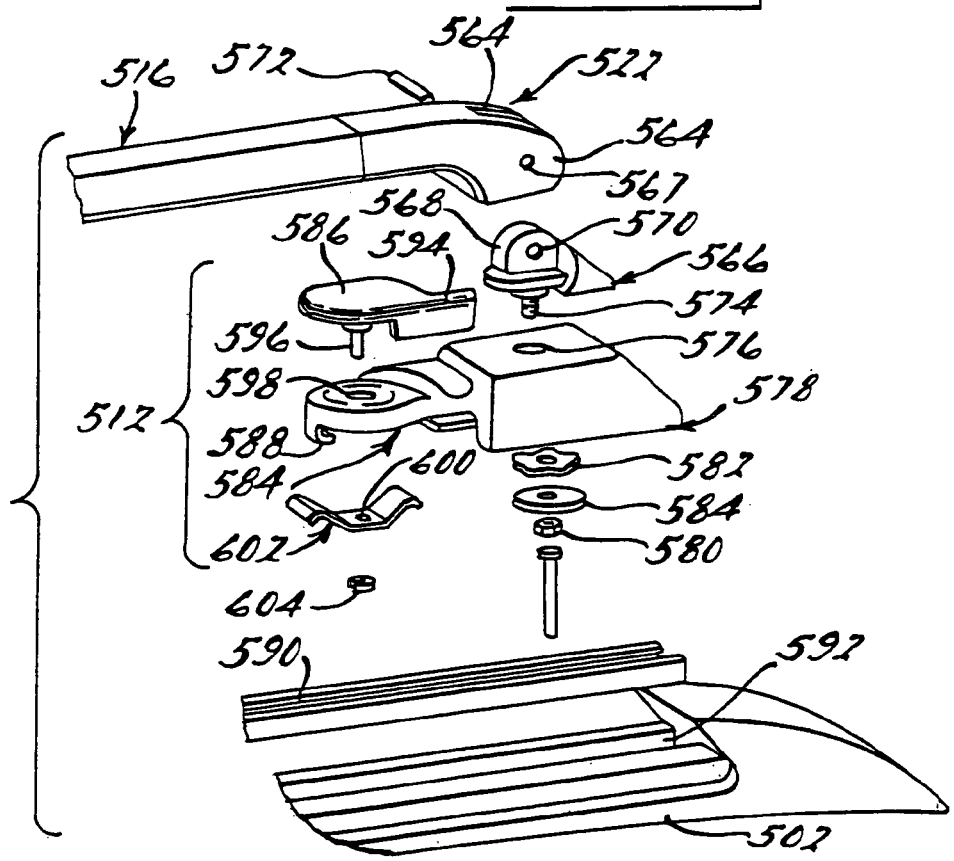

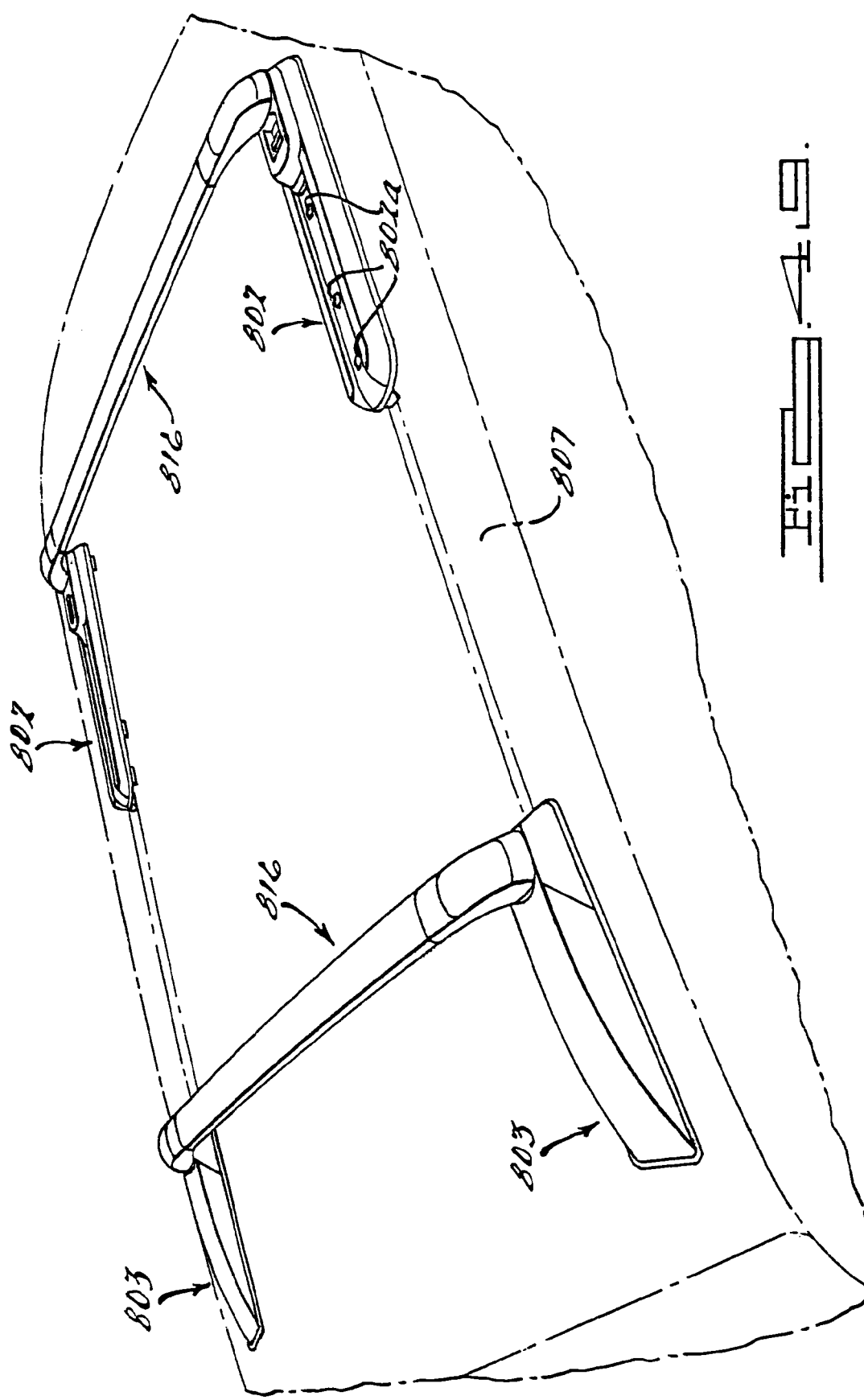

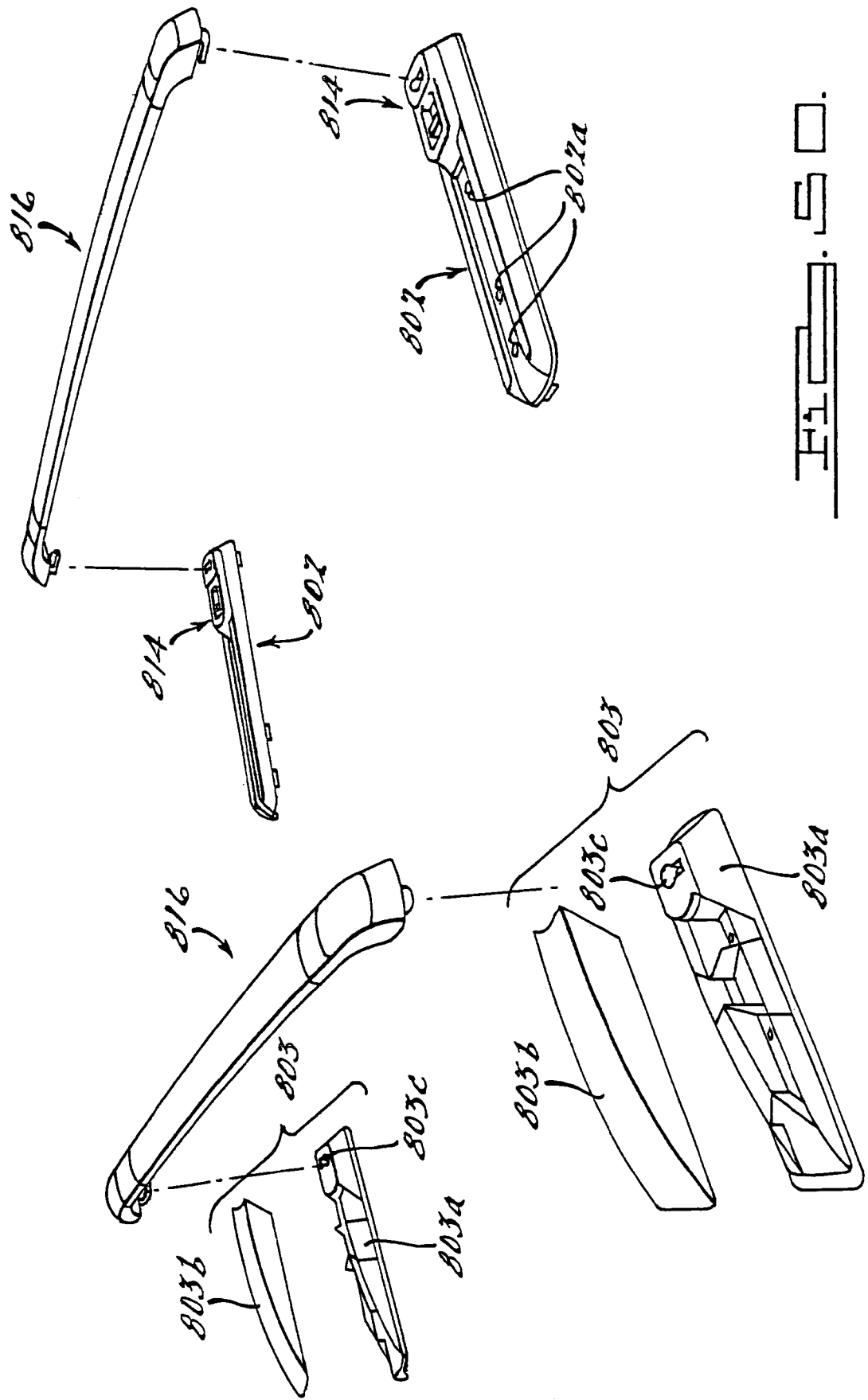

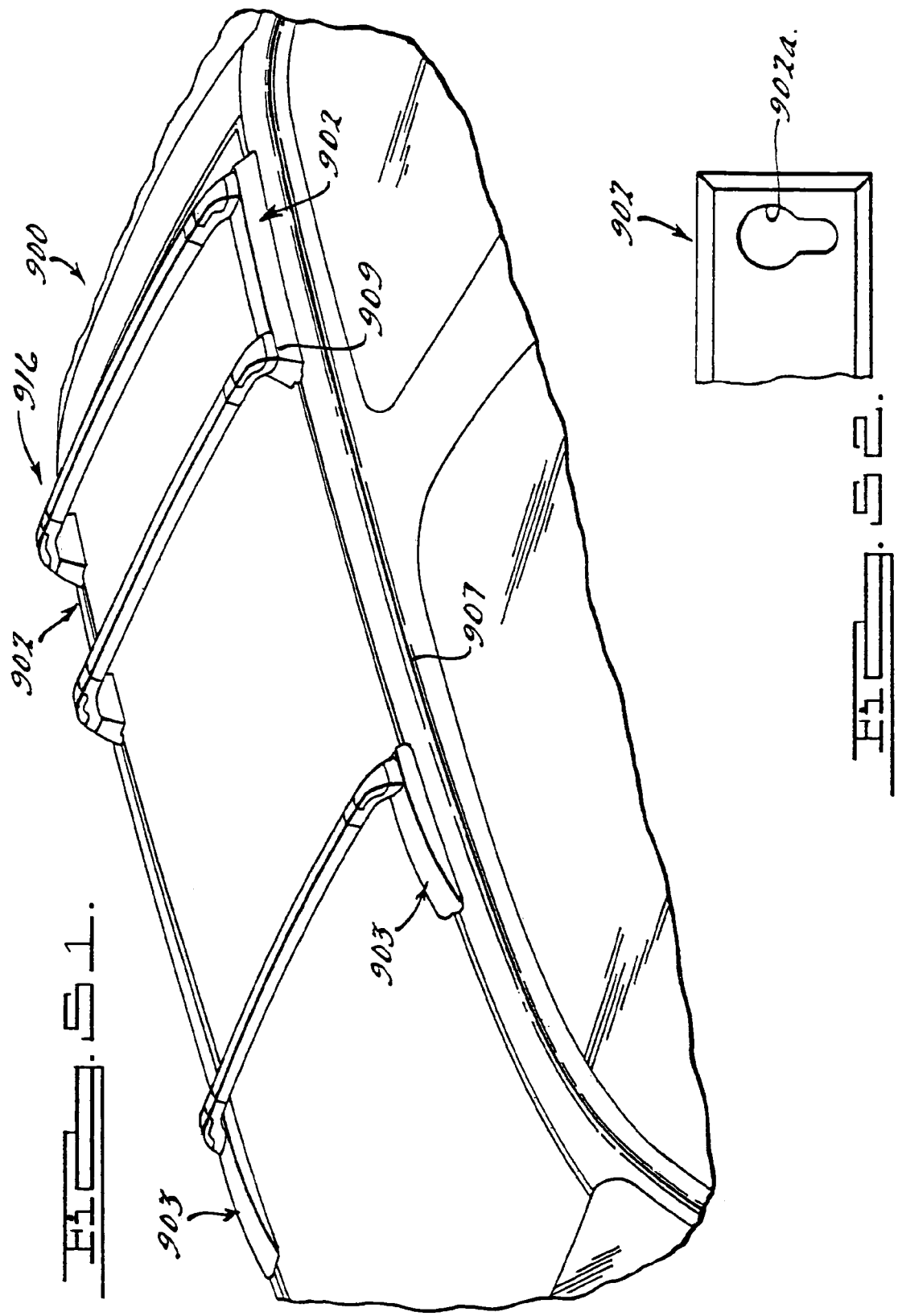

VEHICLE ARTICLE CARRIER HAVING STOWABLE CROSS BARS

CROSS-REFERENCE TO RELATED APPLICATIONS

This application is a divisional of U.S. Ser. No. 10/850,595, filed May 19, 2004, which is a continuation-in-part of U.S. Ser. No. 10/700,334, filed Nov. 3, 2003, which is a continuation-in-part of U.S. Ser. No. 10/700,335, filed Nov. 3, 2003, which is a continuation-in-part of pending U.S. Ser. No. 10/279,285, filed Oct. 24, 2002, which claims the benefit of U.S. Provisional Application No. 60/339,925, filed Nov. 26, 2001. The disclosures of the above applications are incorporated herein by reference.

FIELD OF THE INVENTION

The present invention generally relates to vehicle article carriers such as luggage racks and, more particularly, to a vehicle article carrier having crossbars operable in a first or stowed mode oriented parallel to the longitudinal axis of the vehicle and in a second or article carrying mode oriented perpendicular to the longitudinal axis of the vehicle.

BACKGROUND OF THE INVENTION

Modern automotive vehicles are commonly equipped with article carriers such as luggage racks for supporting various articles externally of the vehicle. Most vehicle article carriers include a pair of siderails laterally spaced apart on the vehicle roof (or trunk) and aligned parallel to the longitudinal axis of the vehicle. Most vehicle article carriers also include two or more crossbars laterally spanning the space between the siderails. The crossbars work in conjunction with the siderails to provide anchor points for securing articles to the carrier.

While such vehicle article carriers perform excellently in terms of article support and the like, there is still room for improvement. For example, vehicle article carrier crossbars can sometimes contribute to wind noise audible to vehicle occupants. Inasmuch as wind noise is generally considered undesirable, minimizing wind noise caused by vehicle article carrier crossbars is an important goal.

One attempt to reduce wind noise caused by vehicle article carrier crossbars has been to improve the aerodynamic characteristics of the crossbars. While some of these attempts have proven helpful in reducing wind noise, even more effective wind noise reduction would be highly desirable. Accordingly, there is a need in the art for a vehicle article carrier having an improved crossbar configuration which further minimizes wind noise audible within the vehicle occupant compartment.

SUMMARY OF THE INVENTION

The above and other objects are provided by a vehicle article carrier including a pair of laterally spaced apart siderails. A pair of crossbars are coupled to the siderails. Each crossbar is operable in a first or stowed mode axially aligned with a siderail and in a second or carrying mode laterally spanning the space between the siderails. In a first embodiment, an orientation assembly interengaging the siderails and crossbars ensures that the crossbars are only oriented in one of the first and second modes. That is, the crossbars are not pivotable through orientations between the spanning position and the stowed position. In a second embodiment, the crossbars are pivotable throughout the range of motion between the spanning position and the stowed position. A separate mechanism is also provided to enable the crossbars to be longitudinally repositioned along the siderail. In a third embodiment, the crossbars include a pivoting latch for securing the crossbar to the siderail. This eliminates a rotatable knob provided in the other embodiments. An actuating member helps facilitate the transition between the spanning and stowed modes. In a fourth embodiment, an alternate latch is employed and the crossbar is both horizontally pivotable and vertically rotatable relative to the siderails.

In one alternative the preferred embodiment of the present invention a vehicle article carrier system is provided in which one of the cross bar assemblies is pivotally coupled to a mounting member disposed on a support wheel at a forward end of the support wheel and the other one of the cross bar assemblies is pivotally coupled to a support assembly at a rear portion of the other one of the support rails. The opposite end of each cross bar assembly includes a locking mechanism having a locking member which can be rotated within a plain generally parallel with the outer body surface of the vehicle. Furthermore, a pair of support assemblies are mounted on each of these support rails at rear portions of each of the support rails, include mechanisms by which each of the support assemblies can be locked at a desired position on the support rails or alternatively loosened to permit repositioning of the support assemblies at a different desired position along the support wheels.

In another alternative preferred embodiment, a vehicle article carrier is disclosed that incorporates a pair of side rail assemblies that can be quickly and easily installed on an outer body vehicle surface, and further in a manner that conceals the mounting hardware used to secure the side rails assemblies to the outer body surface.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

In order to appreciate the manner in which the advantages and objects of the invention are obtained, a more particular description of the invention will be rendered by reference to specific embodiments thereof which are illustrated in the appended drawings. Understanding that these drawings only depict preferred embodiments of the present invention and are not therefore to be considered limiting in scope, the invention will be described and explained with additional specificity and detail through the use of the accompanying drawings in which:

FIG. 5 is a perspective view of the first embodiment siderail and crossbar assembly in a spanning mode;

FIG. 6 is a top view of a second embodiment vehicle article carrier in accordance with the present invention in a spanning mode;

FIG. 7 is a top view of the second embodiment vehicle article carrier in accordance with the present invention in a stowed mode;

FIG. 8 is a top view of the second embodiment vehicle article carrier in accordance with the present invention pivoting between the spanning and stowed modes;

FIG. 9 is a perspective view of a crossbar and a siderail of the second embodiment vehicle article carrier of the present invention in a spanning mode;

FIG. 10 is a perspective view of a crossbar and a siderail of the second embodiment vehicle article carrier of the present invention in a stowed mode;

FIG. 11 is an exploded perspective view of a crossbar and a siderail of the second embodiment vehicle article carrier of the present invention;

FIG. 12 is a perspective view of a third embodiment vehicle article carrier in accordance with the present invention in a spanning mode;

FIG. 14 is a perspective view of the third embodiment vehicle article carrier in accordance with the present invention pivoting between the spanning and stowed modes;

FIG. 15 is a perspective view of a cross bar and siderail of the third embodiment vehicle article carrier of the present invention in a spanning mode;

FIG. 19 is a bottom view of the opposite end of the cross bar shown in FIG. 16;

FIG. 20 is a perspective view of a fourth embodiment vehicle article carrier in accordance with the present invention in a spanning mode;

FIG. 21 is a top view of the fourth embodiment vehicle article carrier in a stowed mode;

FIG. 22 is a perspective view of a securing mechanism of the fourth embodiment vehicle article carrier in a locked mode;

FIG. 23 is a perspective view of the securing mechanism of the fourth embodiment vehicle article carrier in an unlocked mode;

FIG. 24 is an exploded view of the securing mechanism of the fourth embodiment vehicle article carrier;

FIG. 27 is a perspective view of a rotating and pivoting mechanism of the fourth embodiment vehicle article carrier;

FIG. 28 is a cross-sectional view of the rotating and pivoting mechanism of the fourth embodiment vehicle article carrier in a non-rotated state;

FIG. 29 is a cross-sectional view of the rotating and pivoting mechanism of the fourth embodiment vehicle article carrier in a rotated state;

FIG. 30 is an exploded perspective view of still another alternative preferred end support for use with the article carrier of the present invention;

FIG. 31 is a view of a rear portion of the latching member shown in FIG. 30;

FIG. 34 is a perspective view of a vehicle article carrier in accordance with an alternative preferred embodiment of the present invention, showing the cross bar assemblies in their stowed positions;

FIG. 35 is a perspective view of the vehicle article carrier of FIG. 34 but with the cross bar assemblies configured in their operative positions;

FIG. 36 is an exploded perspective view of one of the support members of the vehicle article carrier;

FIG. 37 is an exploded perspective view of one of the support assemblies of the vehicle article carrier which allows lifting as well as pivotal movement of the cross bar assembly secured thereto, and also longitudinal adjustable movement of its associated cross bar assembly;

FIG. 45 is a bottom perspective view of the locking member used with the end support shown in FIG. 41;

FIG. 46 is a side cross sectional view of the end support of FIG. 38 attached to the longitudinally adjustable support assembly shown in FIG. 40, with the locking member in a locked position.

FIG. 49 is a perspective view of an alternative preferred form of the vehicle article carrier;

FIG. 50 is an exploded perspective view of the components of the article carrier of FIG. 49;

FIG. 51 is a perspective view of another alternative preferred form of the article carrier of the present invention;

FIG. 52 is a view of one of the keyed openings used to attach the cross bar to the rear side rail.

DETAILED DESCRIPTION OF THE PREFERRED EMBODIMENTS

The following description of the preferred embodiments is merely exemplary in nature and is in no way intended to limit the invention, its application, or uses.

The present invention is directed towards a vehicle article carrier such as a luggage rack. The vehicle article carrier includes a pair of laterally spaced apart siderails. A pair of crossbars are coupled to the siderails and are operable in one of two modes. In a first mode, the crossbars are stowed in axial alignment with the siderails. In a second mode, the crossbars laterally span the space between the siderails.

Figure 1:
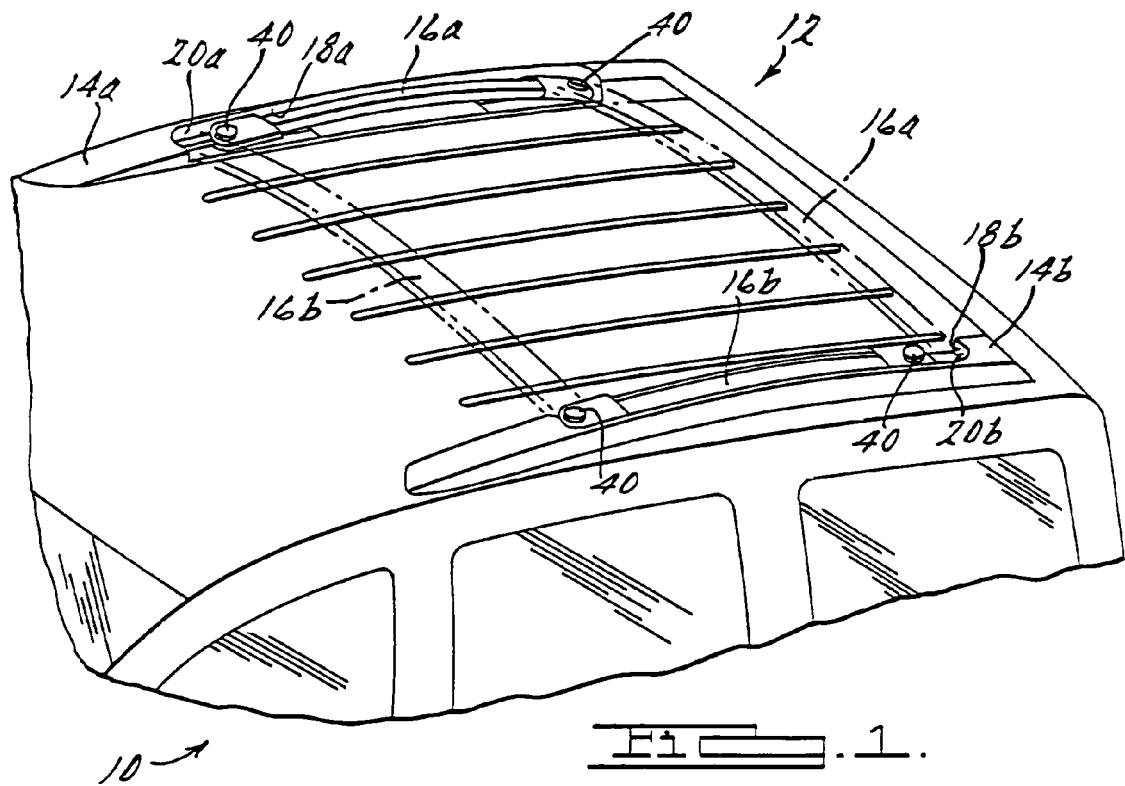
FIG. 1 is a perspective view of a motor vehicle having a vehicle article carrier incorporating the teachings of the present invention mounted thereon.

Turning now to the drawing figures, FIG. 1 illustrates an automotive vehicle in the form of a mini-van generally at 10. A vehicle article carrier 12 is mounted to a roof of the vehicle 10. The vehicle article carrier 12 includes a pair of laterally spaced apart, parallel siderail assemblies 14a and 14b. A pair of crossbar assemblies 16a and 16b are coupled to siderail assemblies 14a and 14b.

Each crossbar assembly 16a, 16b is operable in a first or stowed mode nested within a recessed area 18a, 18b of a siderail assembly 14a, 14b. In the stowed mode, each crossbar assembly 16a, 16b is axially aligned relative to a siderail assembly 14a, 14b. The stowed mode is illustrated in solid lines in FIG. 1.

Each crossbar assembly 16a, 16b is also operable in a second or spanning mode projecting across the space between the siderail assemblies 14a and 14b. In the spanning mode, each crossbar assembly 16a, 16b is laterally aligned relative to the siderail assemblies 14a and 14b. The spanning mode is illustrated in dashed lines in FIG. 1.

To facilitate the transition of the crossbar assemblies 16a and 16b between the stowed mode position and the spanning mode position, gaps 20a and 20b are provided at opposite ends of each recessed area 18a, 18b. The gaps 20a and 20b accommodate one end of a crossbar assembly 16a or 16b in a spanning mode position while the other crossbar assembly 16a or 16b remains in a stowed mode position. In this way, a user may disconnect a stowed crossbar assembly 16a, 16b from one side of the vehicle 10 and reposition it cross-wise to the vehicle without having to walk to the opposite side of the vehicle. The gaps 20a and 20b provide a place for the far end of the crossbar assembly 16a or 16b to rest while the near end is being resecured to the near siderail assembly.

Figure 2:
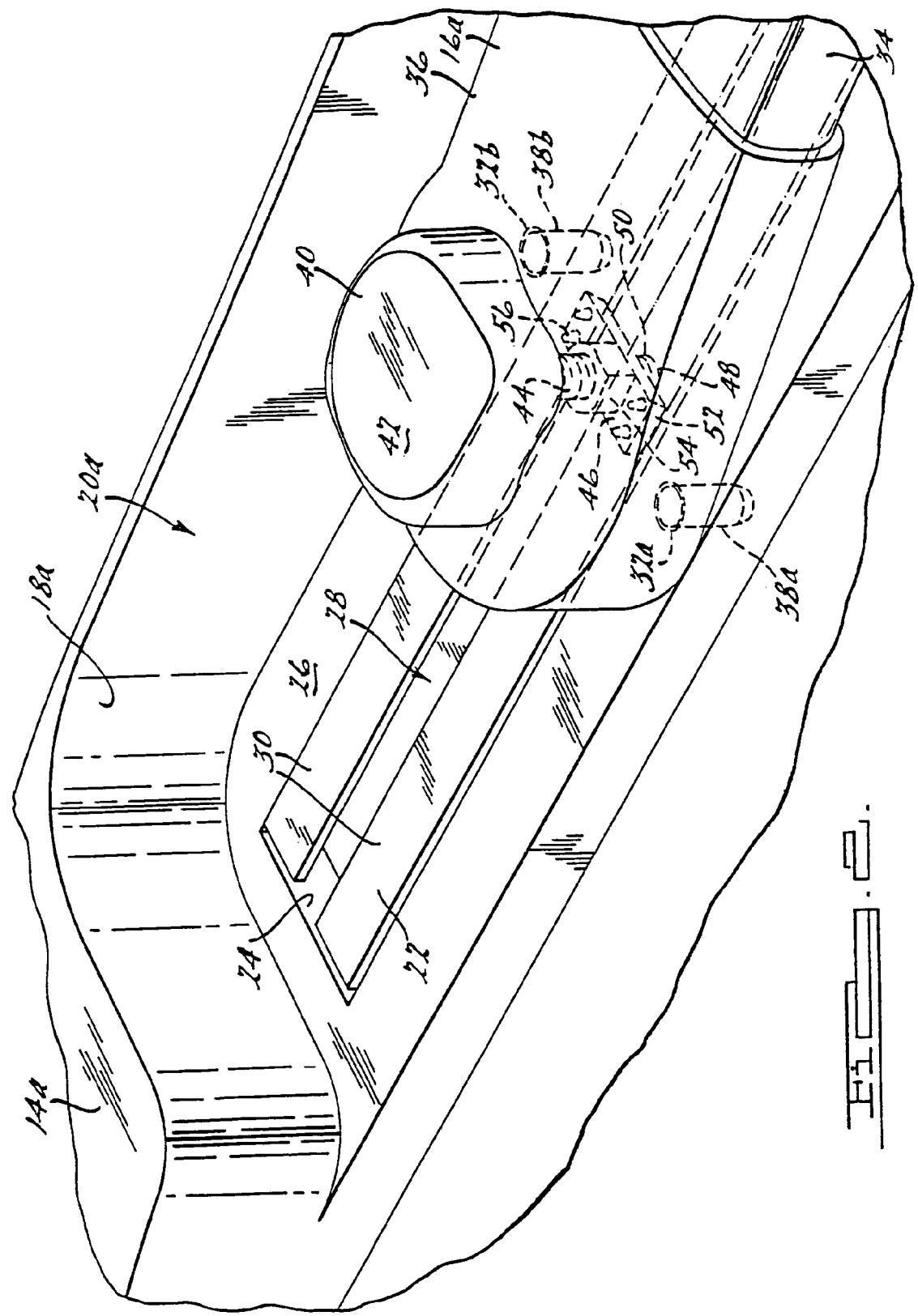
FIG. 2 is a perspective view of a siderail and crossbar assembly according to a first embodiment of the present invention in a stowed mode.

Turning now to FIG. 2, a siderail assembly 14a and crossbar assembly 16a according to a first embodiment are illustrated. While only one end of the siderail assembly 14a and crossbar assembly 16a is illustrated, one skilled in the art should appreciate that the opposite ends thereof are preferably identically configured. Similarly, while only the siderail assembly 14a and crossbar assembly 16a are illustrated, one skilled in the art should appreciate that the other siderail assembly 14b and crossbar assembly 16b are preferably identically configured.

The siderail assembly 14a is preferably formed as an elongated plastic member by a molding process which simultaneously forms the L-shaped recessed area 18a. An elongated metal slat 22 is disposed within a channel 24 formed in the bottom surface 26 of the recessed area 18a. The slat 22 includes an elongated opening in the form of a slot 28. The slot 28 provides access to an interior volume of the slat 22 which is overhung by a pair of opposing lips 30 forming part of the slat 22.

Although the slat 22 may extend along the entire length of the recessed area 18a, it is presently preferred to limit the length or extension to only that amount which is reasonably necessary for mounting anticipated accessories to the siderail assembly 14a. For example, the slat length may be equivalent to five times the width of the end of the crossbar assembly 16a. Although other materials may be used, it is presently preferred to form the slat 22 from extruded aluminum or roll-formed metal.

A pair of laterally spaced apart locating holes 32a and 32b are formed in the bottom surface 26 of the siderail assembly 14a offset from and on opposite sides of the slat 22. The locating holes 32a and 32b are preferably molded in place when the siderail assembly 14a is formed such that an axis interconnecting the holes is essentially orthogonal to the slat 22. If desired, the holes 32a and 32b may alternatively be bored or drilled in place as desired. Also, if desired, a strengthening sleeve, such as a metal cylinder, may be disposed in each locating hole 32a and 32b for added rigidity.

The position of the locating holes 32a and 32b dictate the length of the gap 20a when the crossbar assembly 16a is in a stowed mode position. The gap 20a should be at least long enough to accommodate an end of a crossbar assembly oriented in a spanning mode position while the other crossbar assembly is oriented in a stowed mode position along the same siderail assembly.

The crossbar assembly 16a is preferably formed by a molding process to include an elongated plastic crossbar body 34. Cross bar body 34 can also be formed from extruded aluminum or roll formed from metal. The crossbar assembly 16a also includes an end support 36 mounted to and end of the crossbar body 34. The end support 36 is also preferably formed as a plastic member by a molding process.

The end support 36 includes a pair of spaced apart locating pegs 38a and 38b extending essentially orthogonally from a mounting surface side thereof. The locating pegs 38a and 38b are preferably molded in place so as to be integral with the end support 36 but may alternatively be secured to the end support 36 as discrete members. The locating pegs 38a and 38b are configured to complement the size, shape, spacing and angle of the locating holes 32a and 32b. As such, the locating pegs 38a and 38b may be remove ably inserted within the locating holes 32a and 32b. In this way, the locating pegs 38a and 38b cooperate with the locating holes 32a and 32b to form part of an orientation assembly for orienting the crossbar assembly 16a in the first or stowed mode.

A locking assembly 40 coupled to the crossbar assembly 16a includes a preferably plastic rotatable knob 42 coupled to a preferably metallic threaded member 44 which extends through an opening formed through the end support 36. The threaded member 44 threadingly engages an auto-aligning locking member 46 in the form of a preferably metallic, e.g., aluminum, stamped tap plate or T-lug. As will be described in greater detail below, by rotating the rotatable knob 42 to tighten the threaded member 44 into the locking member 46, the locking member 46 abuttingly engages the underside of the lips 30 of the slat 22 to lock the crossbar assembly 16a to the siderail assembly 14a. By rotating the rotatable knob 42 to loosen the threaded member 44 from the locking member 46, the locking member 46 disengages the lips 30 of the slat 22 and aligns along the axis of the slot 28 to unlock the crossbar assembly 16a from the siderail assembly 14a.

The distal end 48 of the threaded member 44, includes an unsettled thread area 50 to prevent the threaded member 44 from disconnecting from the locking member 46. That is, as relative rotation between the threaded member 44 and locking member 46 occurs, the locking member 46 may migrate toward the distal end 48 of the threaded member 44. However, when the locking member 46 reaches the unsettled thread area 50, the locking member 46 cannot migrate further or inadvertently be twisted off of the threaded member 44.

Figure 3:
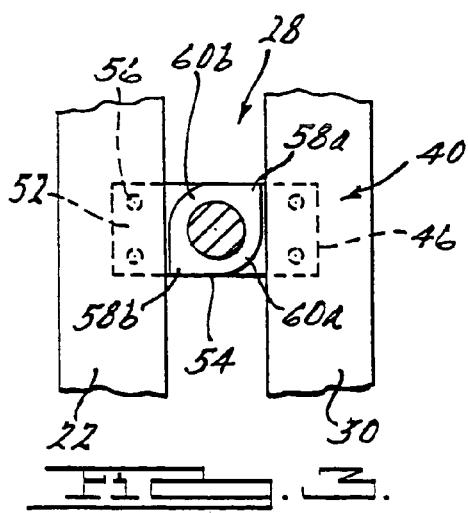
FIG. 3 is a top view of the locking member of the crossbar assembly of the first embodiment of the present invention in a locked mode.
Figure 4:
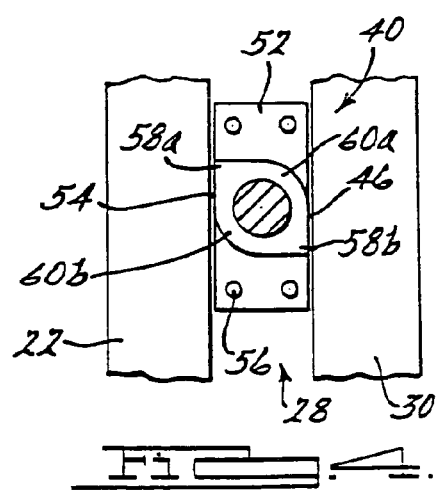
FIG. 4 is a top view of the locking member of the crossbar assembly of the first embodiment of the present invention in an unlocked mode.

Turning now to FIGS. 3 and 4 (and also with continued reference to FIG. 2), the operation of the locking assembly 40 will be described in greater detail. The locking member 46 includes a rectangular base portion 52 having an upstanding orientation portion or collar 54 extending therefrom. The base portion 52 has a width which is less than the width of the slot 28 between the lips 30 of the slat 22. The base portion 52 has a length which is longer than the width of the slot 28. In this way, the locking member 46 can be inserted within the slot 28 and then rotated 90° to underlie the lips 30 and lock in place.

A plurality of conical members or teeth 56 upwardly projecting from the base portion 52 frictionally engage the lips 30 of the slat 22 to prevent relative rotation therebetween. The teeth 56 may be cast in place, machined, or formed by bending up the corners of the base portion 52.

The vertical position of the locking member 46 along the threaded member 44 is controlled such that the orientation portion 54 spans the depth of the slot 28. That is, when the locking member 46 is disposed within the slat 22, the lips 30 of the slat 22 remain adjacent the orientation portion 54. In this way, the orientation portion 54 can interact with the slat 22 to control the orientation of the base portion 52.

More particularly, the orientation portion 54 includes two stops in the form of two oppositely disposed engagement corners 58a and 58b. The orientation portion 54 also includes two oppositely disposed rotation-enabling rounds 60a and 60b. The rounds 60a and 60b allow the locking member 46 to be rotated relative to the slat 22. However, the corners 58a and 58b prevent the locking member 46 from rotating more than 90°. More particularly, during rotation of the threaded member 44, the rounds 60a and 60b rotate relative to the lips 30 of the slat 22. However, at the end of a 90° arc, the engagement corners 58a and 58b abuttingly engage the lips 30. As such, further rotation of the locking member 46 is prevented.

As can be appreciated from the forgoing, the locking member 46 may be easily rotated to a first or engagement position oriented orthogonally relative to the lips 30 or to a second or release position oriented parallel to the lips 30. In the engagement position, the crossbar assembly 16a is locked to the siderail assembly 14a. In the release position, the crossbar assembly 16a is removable from the siderail assembly 14a. After the locking member 46 is released, the crossbar assembly 16a may be lifted from the siderail assembly 14a and repositioned relative thereto.

Turning now to FIG. 5, the crossbar assembly 16b is illustrated in a second or spanning mode relative to the siderail assembly 14a. As illustrated, the end support 36 of the crossbar assembly 16b rests within the gap 20a. Of course, once the other cross bar assembly is removed from the siderail assembly 14a, the spanning crossbar assembly 16b can be positioned anywhere along the length of the slat 22.

In the second or spanning mode, the locating pegs 38a and 38b are inserted within the slot 28 of the slat 22. More particularly, the pegs 38a and 38b are removed from the locating holes 32a and 32b and reoriented 90° relative thereto. The abutting engagement of the pegs 38a and 38b with the lips 30 of the slat 22 maintain the angle of the crossbar assembly 16b relative to the siderail assembly 14a. In this way, the slat 22 cooperates with the locating pegs 38a and 38b to form part of the orientation assembly for orienting the crossbar assembly 16b in the second or spanning mode.

Although it should be clear from the foregoing description, the transition of the crossbar assembly 16b from a stowed mode to a spanning mode and vice versa will be described with reference to FIGS. 1-5. In the stowed mode, the locking assemblies 40 will normally be locked to secure the crossbar assembly 16b to the siderail assembly 14b. The rotatable knob 42 is then rotated in a counter-clockwise direction to loosen the locking member 46 from the lips 30 of the slat 22. Continued counter-clockwise rotation twists the locking member 46 90° from the locked position under the lips 30 to the unlocked position aligned with the slot 28. Abutment of the engagement corners 58a and 58b of the orientation portion 54 with the lips 30 prevents over rotation of the locking member 46.

Once both locking assemblies 40 are unlocked, the crossbar assembly 16b may be lifted away from the siderail assembly 14b and reoriented cross-wise relative thereto. The far end of the crossbar assembly 16b may then be positioned within the gap 20a of the opposite siderail assembly 14a. Simultaneously or thereafter, the near end of the crossbar assembly 16b can be positioned such that the locking member 46 and locating pegs 38a and 38b are inserted within the slot 28. Slight repositioning of the locking member 46 may be performed by manipulation of the rotatable knob 42 if required.

Once the locking member 46 and locating pegs 38a and 38b are properly positioned, the rotatable knob 42 is rotated in a clockwise direction to twist the locking member 46 to an engagement position as controlled by the interaction of engagement corners 58a and 58b with the lips 30. Continued clockwise rotation of the rotatable knob 42 secures the locking member 46 under the lips 30 and locks the crossbar assembly 16b to the siderail assembly 14b.

A similar operation is performed to secure the opposite end of the crossbar assembly 16b to the opposite siderail assembly 14a. To return the crossbar assembly 16b to the stowed mode position, the opposite sequence is performed.

Turning now to FIGS. 6-8, a second embodiment of the present invention is illustrated. The vehicle article carrier 100 includes two laterally spaced apart siderails 102a and 102b. A pair of crossbars 104a and 104b are coupled at opposite ends to the siderails 102a and 102b. The crossbars 104a and 104b are operable in a first or spanning mode, as illustrated in FIG. 6, extending across the space between the siderails 102a and 102b, and also in a second or stowed mode, as illustrated in FIG. 7, axially aligned with the siderails 102a and 102b.

As illustrated in FIG. 8, to facilitate the transition between the spanning mode and the stowed mode, the crossbars 104a and 104b are pivotally coupled at one end to the siderails 102a and 102b. More particularly, the crossbar 104a includes a pivot mechanism 106a pivotally coupled to the siderail 102b. Similarly, the crossbar 104b includes a pivot mechanism 106b pivotally coupled to the siderail 102a.

A securing mechanism 108a is provided at the opposite end of the crossbar 104a for securing the crossbar 104a to the siderail 102b in a stowed mode (see FIG. 7) and to the siderail 102a in a spanning mode (see FIG. 6). Similarly, a securing mechanism 108b is provided at the opposite end of the crossbar 104b for securing the crossbar 104b to the siderail 102a in a stowed mode (see FIG. 7) and to the siderail 102b in a spanning mode (see FIG. 6). An exemplary securing mechanism 108a is illustrated in greater detail in FIGS. 9-11.

As shown in FIGS. 9-11, the securing mechanism 108a interconnects a shroud 110a of the crossbar 104a with a moveable mount 112b secured to the siderail 102b. The shroud 110a is secured to the crossbar 104a by at least one fixing member 111a preferably in the form of a screw. The shroud 110a includes a slotted opening 114a providing a pair of spaced apart shroud arms for sandwiching a tab 116b of the moveable mount 112b therebetween. A fastening member preferably in the form of a threaded shaft 118a passes through the shroud 110a and tab 116b to secure the two together. A retention member preferably in the form of a threaded nut 120a engages the threaded shaft 118a to fix the crossbar 104a to the siderail 102b. A knob 122a formed at an opposite end of the threaded shaft 118a relative to the nut 120a facilitates turning of the threaded shaft 118a to tighten or loosen the connection with the threaded nut 120a. Preferably, the nut 120a is fixedly secured to the shroud 110a so as to remain coupled to the shroud 110a even after the shaft 118a is disengaged. In this way, the shaft 118a can be easily engaged and disengaged from the nut 120a before and after pivoting the crossbar 104a between the stowed and spanning positions. Although not illustrated, one skilled in the art will appreciate that the securing mechanism 108b is preferably configured identically to the securing mechanism 108a.

The moveable mount 112b is preferably slideably secured to the siderail 102b. More particularly, a fixing member in the form of a threaded shaft 123b selectively secures the moveable mount 112b along the siderail 102b. An anchor in the form of a tapped plate 124b threadingly engages the threaded shaft 123b and frictionally engages an inner surface of a pair of opposed lips 125b defining an elongated slot 126b in the siderail 102b. A T-shaped lug 127b is preferably integrally provided along an edge of the moveable mount 112b to slidingly accommodate the lips 125b while residing within the slot 126b. An orifice 128b provided in the interior of the moveable mount 112b accommodates a knob 129b affixed to the threaded shaft 123b opposite the tapped plate 124b. By turning the knob 129b, the threaded shaft 123b releases the frictional engagement of the tapped plate 124b with the lips 125b thereby enabling sliding movement of the moveable mount 112b along the siderail 102b.

Another moveable mount 112b' is also slideably secured to the siderail 102b. The moveable mount 112b' is preferably configured identical to that of the moveable mount 112b. Similarly, as illustrated in FIGS. 6-8, two moveable mounts 112a and 112a' are slideably secured to the siderail 102a. The moveable mounts 112a and 112a' are preferably configured identical to that of the moveable mounts 112b and 112b'. By providing the moveable mounts 112, the crossbars 104a and 104b can be selectively positioned along the siderails 102a and 102b while in the spanning mode.

A pivoting mechanism 106a interconnects a shroud 132a of the crossbar 104a with the moveable mount 112b' secured to the siderail 102b. The shroud 132a is secured to the crossbar 104a by at least one fixing member 134a in the form of a screw. The shroud 132a includes a slotted opening 136a providing a pair of shroud arms for sandwiching a tab 116b' of the moveable mount 112b' therein. A pivot member in the form of a partially threaded shaft 140a passes through the shroud 132a and tab 116b' to secure the two together. A threaded nut 142a engages the threaded shaft 140a to fix the two in place. Although not illustrated, one skilled in the art will appreciate that the pivoting mechanism 106b is preferably configured identically to the pivoting mechanism 106a.

Figure 13:
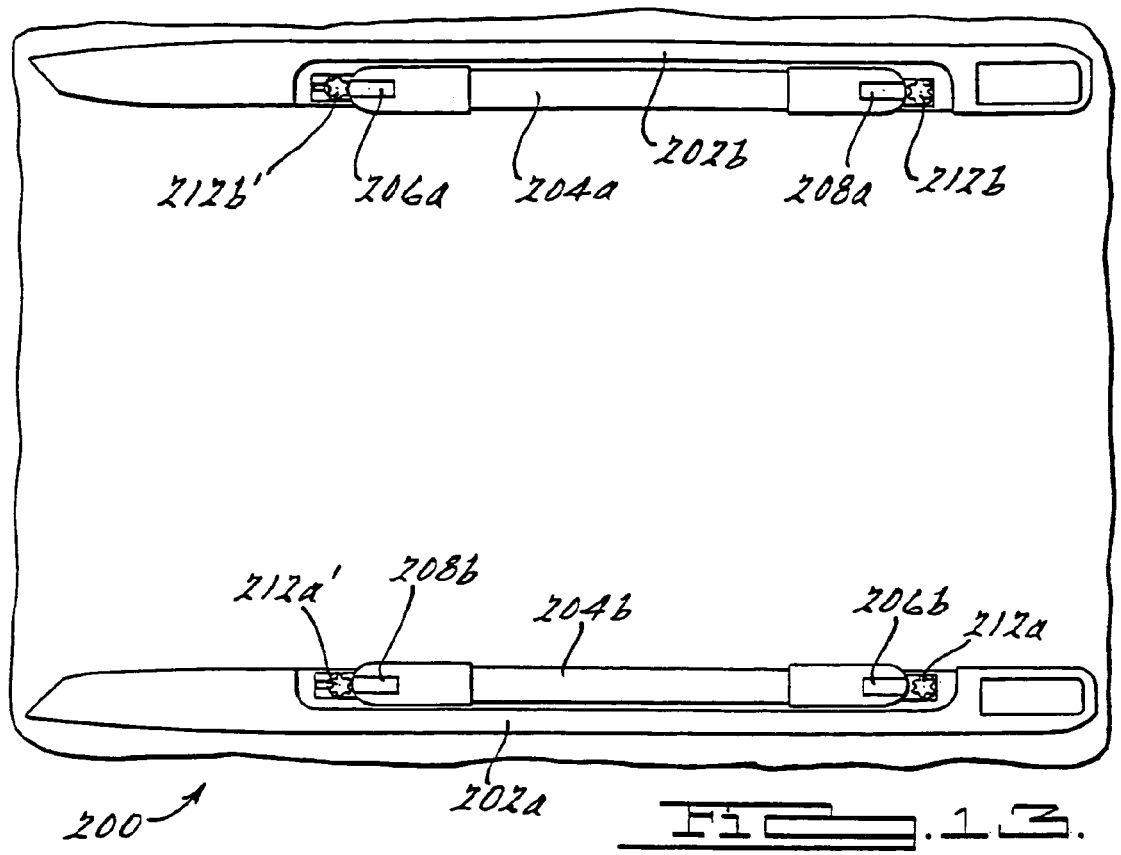
FIG. 13 is a top view of the third embodiment vehicle article carrier in accordance with the present invention in a stowed mode.
Figure 13:
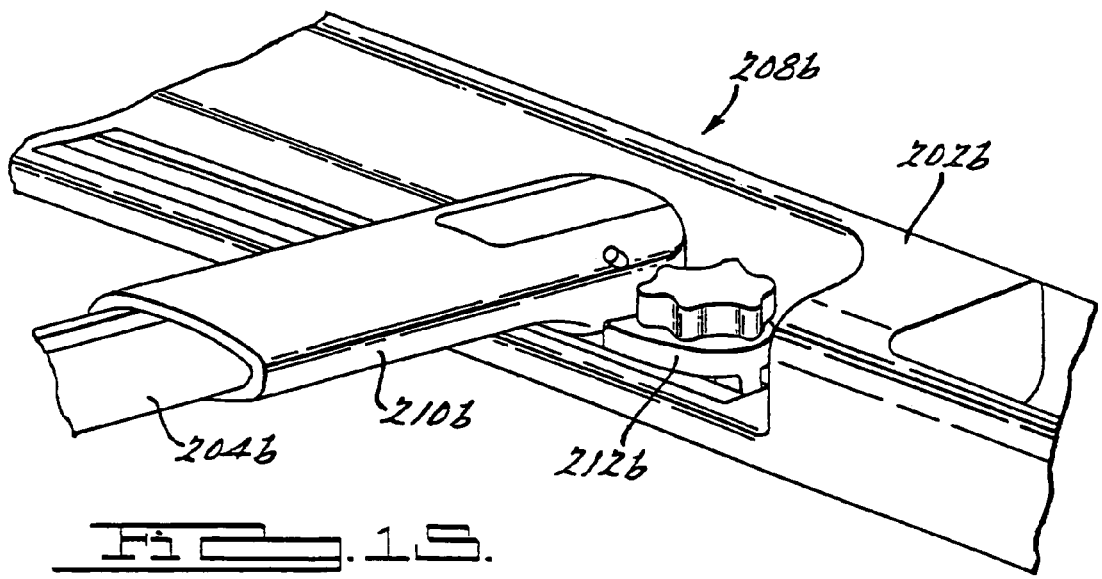

Turning now to FIGS. 12-14 a third embodiment of the present invention is illustrated. The vehicle article carrier 200 includes two laterally spaced apart siderails 202a and 202b. A pair of crossbars 204a and 204b are coupled at opposite ends to the siderails 202a and 202b. The crossbars 204a and 204b are operable in a first or spanning mode, as illustrated in FIG. 12, extending across the space between the siderails 202a and 202b, and also in a second or stowed mode, as illustrated in FIG. 13, axially aligned with the siderails 202a and 202b.

As illustrated in FIG. 14, to facilitate the transition between the spanning mode and the stowed mode, the crossbars 204a and 204b are pivotally coupled to the siderails 202a and 202b. More particularly, the crossbar 204a includes a pivoting latch mechanism 206a pivotally coupled to the siderail 202b. Similarly, the crossbar 204b includes a pivoting latch mechanism 206b pivotally coupled to the siderail 202a.

A securing mechanism 208a is provided at the opposite end of the crossbar 204a relative to the pivoting latch mechanism 206a for securing the crossbar 204a to the siderail 202b in a stowed mode (see FIG. 13) and to the siderail 202a in a spanning mode (see FIG. 12). Similarly, a securing mechanism 208b is provided at the opposite end of the crossbar 204b relative to the pivoting latch mechanism 206b for securing the crossbar 204b to the siderail 202a in a stowed mode (see FIG. 13) and to the siderail 202b in a spanning mode (see FIG. 12). An exemplary securing mechanism 208b is illustrated in greater detail in FIGS. 15-16.

Figures 16, 17, 18:
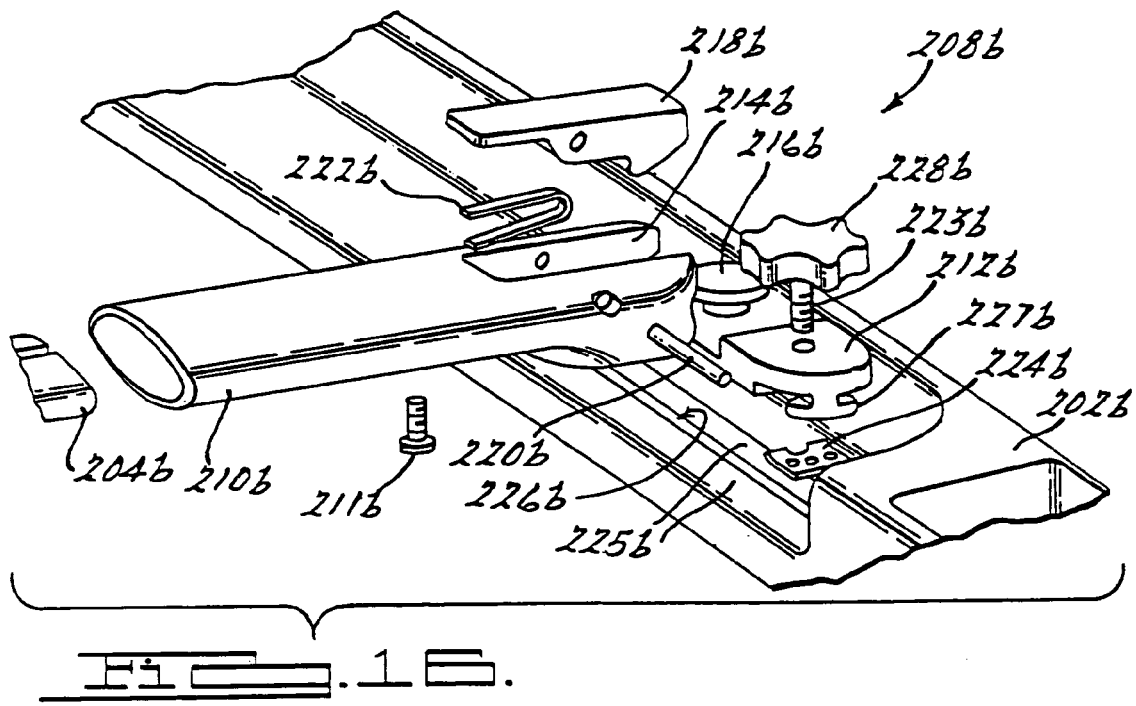
FIG. 16 is an exploded perspective view of a cross bar and siderail of the third embodiment vehicle article carrier of the present invention.
FIG. 17 is a bottom view of the cross bar and siderail of FIG. 16 in an extended mode.
FIG. 18 is a bottom view of the cross bar and siderail of FIG. 16 in a retracted mode.
Figure 25:
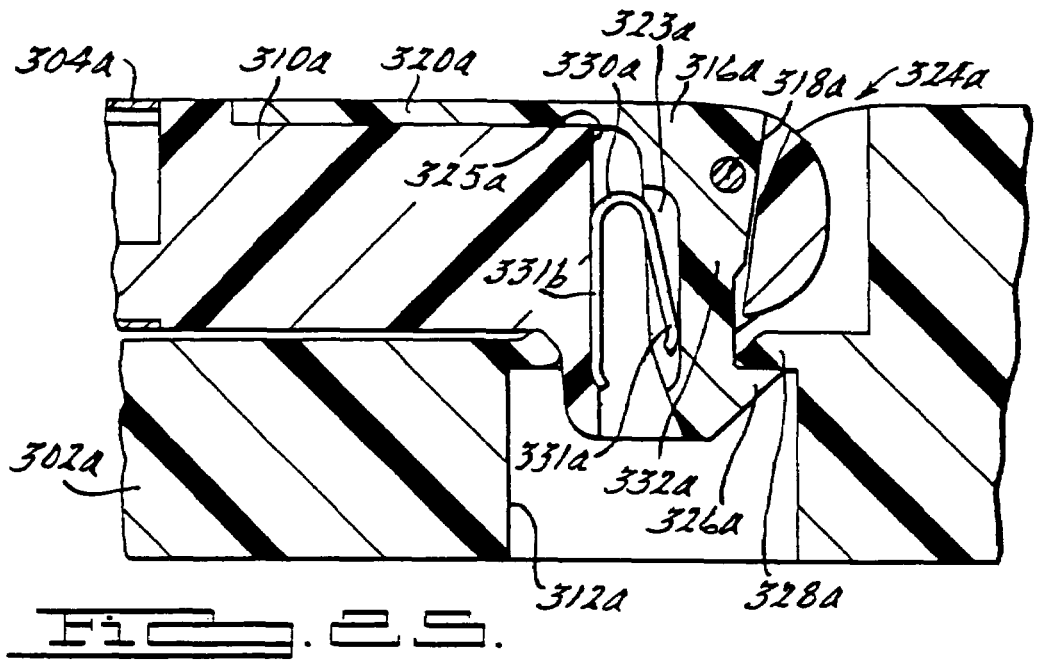
FIG. 25 is a cross-sectional view of the securing mechanism of the fourth embodiment vehicle article carrier in a locked mode.
Figure 26:
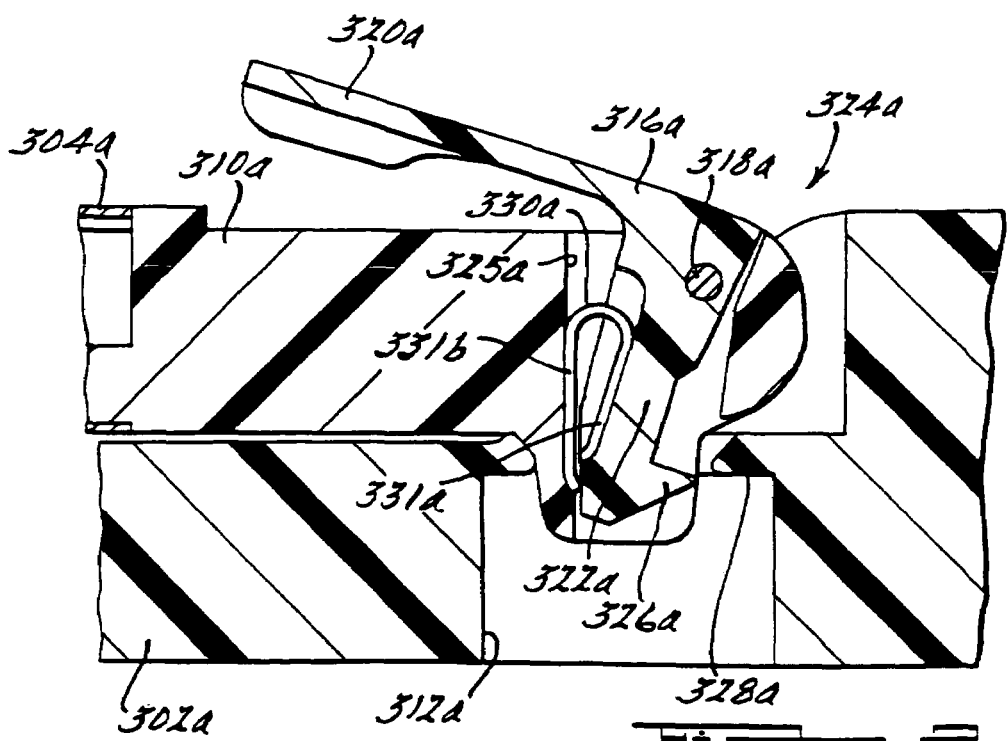
FIG. 26 is a cross-sectional view of the securing mechanism of the fourth embodiment vehicle article carrier in an unlocked mode.

As shown in FIGS. 15-18, the securing mechanism 208b interconnects an end support shroud 210b of the crossbar 204b with a moveable mount 212b secured within a recess of the siderail 202b. The end support 210b is secured to the crossbar 204b in a telescoping manner by at least one fixing member 211b in the form of a screw. The fixing member 211b is fixed relative to the crossbar 204b but the end support 210b is moveable relative to both the fixing member 211b and the crossbar 204b. As such, the end support 210b can be translated between an extended or engaged mode, as illustrated in FIG. 17, and a retracted or disengaged mode, as illustrated in FIG. 18. A slot 213b formed in the end support 210b accommodates such movement.

The end support 210b includes a slotted opening 214b for enveloping a mushroom-shaped nub 216b of the moveable mount 212b therein. A base 217b of the end support 210b slides under the top and on either side of the trunk of the mushroom-shaped nub 216b while the walls of the shroud adjacent the opening 214b abut the sides of the nub 216b. A fastening member in the form of a pivotable latch 218b pivotally resides within the slotted opening 214b and is operable in a locked mode to engage the nub 216b and an unlocked mode to release the nub 216b. An axle 220b secures the latch 218b to the end support 210b and serves as a pivot for the latch 218b. A biasing member in the form of a spring clip 222b nests within the opening 214b and urges the latch 218b toward the locked mode. To disengage the latch 218b from the nub 216b, the bias of the spring 222b is overcome by depressing the inboard end of the latch which allows the outboard end of the latch to lift off and release the nub 216b. Once released from the nub 216b, the shroud may be translated away from the nub 216b to provide clearance for the cross bar 204b to pivot.

One skilled in the art will appreciate that the securing mechanism 208a is preferably configured identically to the securing mechanism 208b. Similarly, The securing mechanisms 206a and 206b are preferably configured identically to the securing mechanisms 208a and 208b with the exception of the translatable end support. Referring to FIG. 19, the securing mechanism 206b is illustrated. The end support 210b' is fixedly secured to the crossbar 204b by at least one fixing member 211b' in the form of a screw. No slot is provided in the end support 210b'. In this way, the crossbar 204b is provided with one fixed end support 210b' and one translatable end support 210b (See FIGS. 17 and 18). Likewise, the crossbar 204a is provided with one fixed end support 210a' and one translatable end support 210a (see FIG. 12).

Referring again to FIGS. 15 and 16, the moveable mount 212b is preferably slideably secured to the siderail 202b. More particularly, a fixing member in the form of a threaded shaft 223b selectively secures the moveable mount 212b along the siderail 202b. An anchor in the form of a tapped plate 224b threadingly engages the threaded shaft 223b and frictionally engages an inner surface of a pair of opposed lips 225b defining an elongated slot 226b in the siderail 202b. A t-shaped lug 227b is preferably integrally provided along an edge of the moveable mount 212b to slidingly accommodate the lips 225b while residing within the slot 226b. A knob 228b is provided on the threaded shaft 223b opposite the tapped plate 224b. By turning the knob 228b, the threaded shaft 223b releases the frictional engagement of the tapped plate 224b with the lips 225b thereby enabling sliding movement of the moveable mount 212b along the siderail 202b.

Referring again to FIGS. 12-14, another moveable mount 212b' is also slideably secured to the siderail 202b. The moveable mount 212b' is preferably configured identically to the moveable mount 212b. Similarly, two moveable mounts 212a and 212a' are slideably secured to the siderail 202a. The moveable mounts 212a and 212a' are preferably configured identically to the moveable mounts 212b and 212b'. By providing the moveable mounts 212, the crossbars 204a and 204b can be selectively positioned along the siderails 202a and 202b while in the spanning mode.

Referring collectively to FIGS. 12-19, to reposition the crossbars from a stowed mode to a spanning mode, one securing mechanism 208 of each crossbar is disengaged from a nub and each cross bar is pivoted towards the spanning position about the opposite securing mechanism 206. Each crossbar 204 is also translated such that the end of each crossbar 204 is laterally offset from a nub 216 yet essentially perpendicular to the siderails 202. To accommodate the translation movement, one end support 210 telescopically retracts onto each crossbar 204. The securing mechanism 208 of each crossbar 204 is then positioned adjacent to a nub 216, the crossbar is translated in an opposite direction to move the securing mechanism 208 over top of the nub 216, and subsequently secured thereto with a latch 218.

Turning now to FIGS. 20 and 21, yet another embodiment of the present invention is illustrated. The vehicle article carrier 300 includes two laterally spaced apart support rails forming siderails 302a and 302b. A pair of crossbars 304a and 304b are coupled at opposite ends to the siderails 302a and 302b. The crossbars 304a and 304b are operable in a first or spanning mode, as illustrated in FIG. 20, extending across the space between the siderails 302a and 302b, and also in a second or stowed mode, as illustrated in FIG. 21, axially aligned with the siderails 302a and 302b.

To facilitate the transition between the spanning mode and the stowed mode, the crossbars 304a and 304b are rotatably and pivotally coupled to the siderails 302a and 302b. More particularly, the crossbar 304a includes a rotating and pivoting mechanism 306a pivotally coupled to the siderail 302b. Similarly, the crossbar 304b includes a rotating and pivoting mechanism 306b pivotally coupled to the siderail 302a.

A securing mechanism 308a is provided at the opposite end of the crossbar 304a relative to the pivoting mechanism 306a for securing the crossbar 304a to the siderail 302b in a stowed mode (see FIG. 21) and to the siderail 302a in a spanning mode (see FIG. 20). Similarly, a securing mechanism 308b is provided at the opposite end of the crossbar 304b relative to the pivoting mechanism 306b for securing the crossbar 304b to the siderail 302a in a stowed mode (see FIG. 21) and to the siderail 302b in a spanning mode (see FIG. 20). An exemplary securing mechanism 308a is illustrated in greater detail in FIGS. 22-26.

As shown in FIGS. 22-26, the securing mechanism 308a interconnects an end support 310a of the crossbar 304a with a mounting portion 312a of the siderail 302a. The end support 310a is preferably formed integrally with a lower portion of the crossbar 304a. The end support 310a includes a recessor pocket 314a accommodating a complementary shaped latch 316a therein.

The latch 316a is preferably pivotally mounted within the end support 310a by an axle 318a forming a pivot. The latch 316a is operable in a locked mode engaged with the siderail 302a (see FIGS. 22 and 25) and in an unlocked mode disengaged from the siderail 302a (see FIGS. 23 and 26). A handle 320a of the latch extends along an upper surface of the end support 310a and is oriented generally orthogonal to an arm 322a of the latch 316a. The handle 320a serves as a user operated lever to move the latch 316a between the locked and unlocked modes.

The arm 322a extends through a partially slotted opening 324a formed through the end support 310a. The slotted opening 324a is sized to accommodate the desired range of motion during pivoting of the latch 316a about the axle 318a. The arm 322a includes a catch 326a for frictionally engaging a lip 328a of the mounting portion 312a of the siderail 302a when the latch 316a is in the locked mode.

A biasing member in the form of a spring clip 330a is disposed in the slotted opening and one leg 331a is received in a notch 323a of the latch 316a. This helps to hold the spring clip 330a properly orientated within the slotted opening 324a. The other leg 331b of the spring clip 330a abuts a wall portion 325a of the end support 310a. The spring clip 330a urges the latch 316a towards the closed mode such that the catch 326a is biased to engage the lip 328a. To release the latch 316a, the bias of the spring clip 330a is overcome by lifting the handle 320a, the arm 322a pivots away from the lip 328a, and the catch 326a disengages therefrom. The crossbar 304a can then be lifted away from the mounting portion 312a and rotated relative to the siderail 302a. Although not illustrated, one skilled in the art should appreciate that the other securing mechanism 308b is preferably configured identically to the securing mechanism 308a.

Turning now to FIGS. 27-29, the rotating and pivoting mechanism 306a will be described. The mechanism 306a includes an endpiece 340a preferably formed integrally with a lower portion of the crossbar 304a. A guide member in the form of a pin 342a is positioned within a opening 344a formed in the endpiece 340a. The opening 344a includes a lower portion $344a_1$ that is preferably shaped as a triangular slot, or a slot of non-constant cross sectional area, to allow pivoting of the crossbar 304a relative to the siderail 302b and pin 342a while simultaneously preventing rotation of the crossbar 304a about its own longitudinal axis. The rotation of the crossbar 304a about its own longitudinal axis is accomplished by the abutting engagement of the pin 342a with the walls of the opening 344a.

The lower portion of the endpiece 340a is partially spherically shaped to provide a radiused surface 346a. The radiused surface 346a nests within a complimentary shaped dish 348b secured within a cavity 350b of the siderail 302b. An orifice 352b is provided through the dish 348b to accommodate the pin 342a therein. The radiused surface 346a and dish 348b cooperate to control the pivoting and rotating of the crossbar 304a relative to the siderail 302b.

While not illustrated, one skilled in the art should appreciate that the other rotating and pivoting mechanism 306b is preferably formed identically to the rotating and pivoting mechanism 306a.

Referring now to FIG. 30, an end support 400 in accordance with an alternative preferred embodiment of the present invention is shown. The end support 400 forms a securing mechanism for latching a cross bar 402 to either mounting portion 312a or 312b of the support rails 302a and 302b, respectively (FIGS. 20 and 21). Cross bar 402 itself is otherwise identical in construction to cross bars 304a and 304b shown in FIGS. 20 and 21.

The end support 400 includes an integrally formed housing 404 which is fixedly secured to an outermost end of the cross bar 400 in a conventional manner, such as by a threaded fastening element (not shown). Disposed on, or within, the housing 404 is an actuating member 406, a latching member 408 and a resilient bumper member 410. Biasing members 412 and 414 are also disposed within the housing 404, and will be described in greater detail momentarily.

Referring further to FIG. 30, the actuating member 406 forms a lever having a graspable portion 416 and a mounting structure 418. The graspable portion 416 rests within a recessed portion 420 of an upper portion 422 of the housing 404. The mounting structure 418 is pivotally secured to the housing 404 via a pivot pin 424 that extends through a pair of aligned openings 426 in the mounting structure 418. As such, the actuating member 406 can pivot, relative to the housing 404, between a closed position and an open position. The mounting structure 418 also includes a pair of arcuate guide surfaces 428, the function of which will be discussed momentarily.

A lower portion 430 of the housing 404 extends elevationally below an opening 432 in the upper portion 422 of the housing. Within the opening 432 is disposed the latching member 408. The latching member 408 includes a pair of aligned openings 434 at an upper end 436, a pair of arcuate surfaces 438 at the upper end 436, and a hook or latch 440 at a lower end 442. With brief reference to FIG. 31, the latching member 408 is shown to also include a slot 444 formed therein. The latching member 408 is also pivotally secured to the housing 404 via the pivot pin 424 and is able to pivot between latched and unlatched positions relative to the mounting portions 312a or 312b.

With reference again to FIG. 30, the resilient bumper member 410 can be seen to include a flange 446 which allows the bumper member 410 to be press fit through an opening 448 in the lower portion 430 of the housing 404. The bumper member 410 prevents marring or scratching of the outer body surface of the vehicle in the event the user accidentally drops the housing 404 while moving the cross bar 402 between the stowed and operative positions. The bumper member 410 may be made from rubber or any other suitable material that will not scratch or mar a painted surface upon contact therewith.

Figure 32:
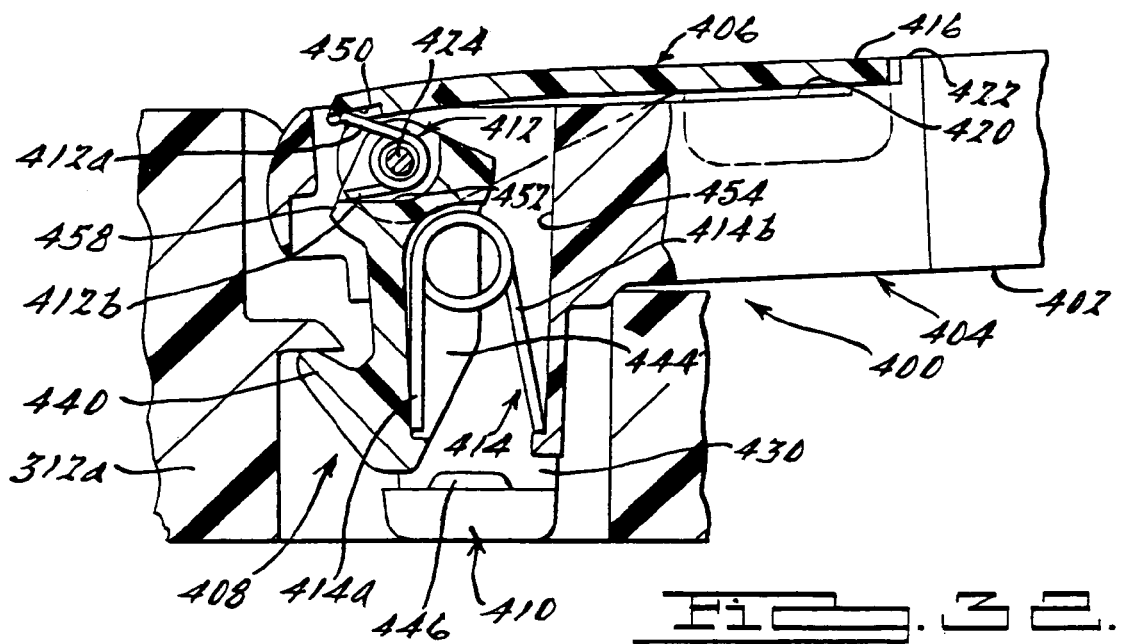
FIG. 32 is a side cross sectional view of the assembled end support of FIG. 30 showing the end support in the latched orientation relative to one of the siderails.

Referring to FIGS. 30 and 32, biasing member 412 forms a torsion spring that is placed with one leg 412a against an inner surface 450 of the actuating member 406 and the other leg 412b against a surface 452 of the actuating member 406. The biasing member 412 thus helps to maintain the actuating member 406 within the recessed area 420 of the housing 404 when the actuating member is in its closed position. Biasing member 414 is placed within the lower portion 430 of the housing 404 with one leg 414a in the slot 444 of the latching member 408 and the other leg 414b against the wall surface 454 of the lower portion 430 of the housing 404. The biasing member 414 serves to provide a constant biasing force which tends to bias the latching member 408 into engagement with the mounting portion 312a or 312b of one of the other support rails 302a or 302b when the housing 404 is latched to one of the mounting portions.

Figure 33:
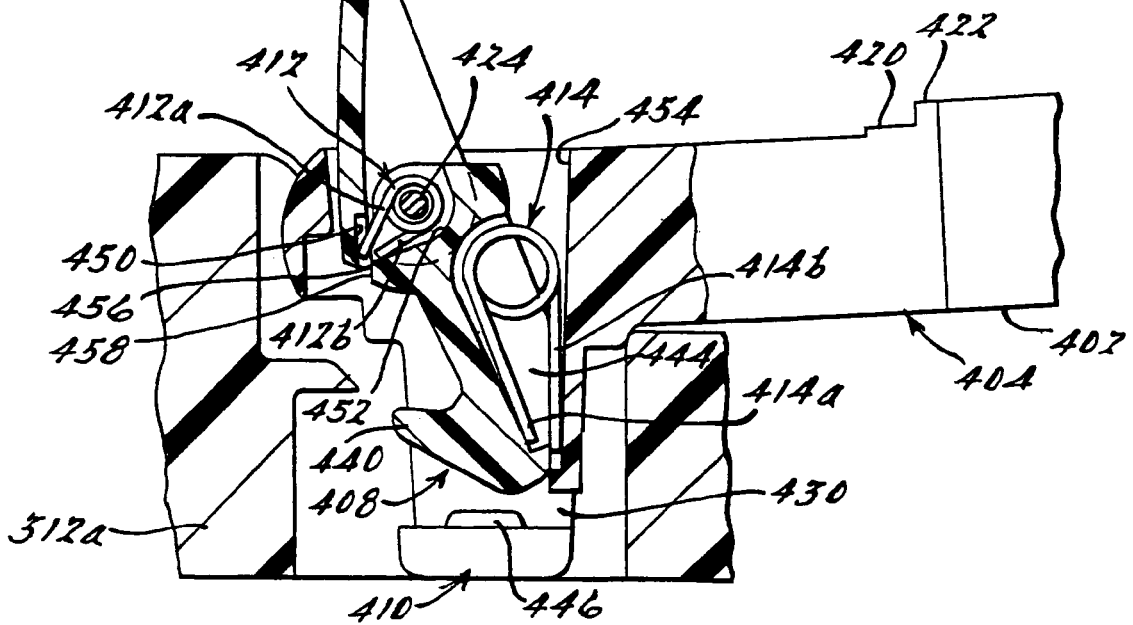
FIG. 33 is a view of the end support of FIG. 32 with the latching member moved into the unlatched position.

Referring now to FIGS. 32 and 33, the housing 404 is shown in latched and unlatched positions, respectively. Referring specifically to FIG. 32, when in the latched position, the actuating member 406 is in the closed position with the graspable portion 416 resting within the recess 420 in the upper portion 422 of the housing 404. The hook portion 440 of the latching member 408 is engaged with the mounting portion 312a of, in this example, support rail 302a.

In FIG. 33 the actuating member 406 has been moved to the open position. During this movement, an edge portion 456 of the actuating member 406 contacts an edge 458 of the latching member 408 and urges the latching member rotationally into an unlatched position relative to the mounting portion 312a of the support rail 302a. During this movement the curved surfaces 428 of the mounting portion 418 ride within the arcuate surfaces 438 of the latching member 408. From FIG. 32 it can be seen that the actuating member 406 is able to rotate a slight degree (preferably about 15-25 degrees), before contacting edge 458 and beginning to unlatch the latching member 408. Rotating the actuating member 406 after contacting edge 458 results in the actuating member beginning to unlatch the actuating member 408, and the additional biasing force of biasing member 414 is overcome as the user rotates the actuating member fully into the position shown in FIG. 33.

This pivotal securing of the actuating member 406 to the latching member 408 provides the benefit that the actuating member is able to be moved into a position perpendicular, or substantially perpendicular, to the upper portion 422 of the housing 404, providing the user with a more natural "feel" that the actuating member is in its fully open position. The biasing force provided by biasing member 412 provides a slight biasing force that causes the actuating member 406 to be immediately snapped back into the closed position once the operator releases the actuating member. It will also be appreciated that the arcuate surfaces 438 on the latching member 408 could be formed with short flat portions or protrusions that form detents to hold the actuating member in the open position of FIG. 33 once the user fully opens the actuating member 406.

Thus, a vehicle article carrier is provided which operates in two modes. In a first mode, the crossbars are stowed such that each lies parallel to a siderail. This mode reduces wind noise from the vehicle article carrier. In a second mode, the crossbars are oriented cross-wise to the longitudinal axis of the vehicle to span the space between the siderails and provide a support structure for carrying desired loads.

Referring to FIG. 34, there is shown another vehicle article carrier 500 in accordance with yet another alternative preferred embodiment of the present invention. The vehicle article carrier 500 is similar to the embodiments described herein and includes a pair of support rails 502 that are disposed parallel to one another on an outer body surface 504 of the motor vehicle. Each support rail 502 has a channel 506 formed therein. Fixed supports 508 and 510 are secured to the support rails 502 and are not movable relative to the support rails 502. Support assemblies 512 and 514, however, are movable along the channels 506 of the support rails 502, as will be explained in greater detail momentarily.

With further reference to FIG. 34, cross bar assemblies 516 and 518 are shown in their "stowed" positions. Cross bar assembly 516 includes a releasable end support 520 and a pivoting end support 522. Cross bar assembly 518, however, includes a pivoting end support 524 and a releasable end support 526. The construction of end supports 520 and 526 are identical, and as such, only the construction of releasable end support 520 will be described.

With brief reference to FIG. 35, the vehicle article carrier 500 is shown with the cross bar assemblies 516 and 518 pivoted into their operative positions. Support assemblies 512 and 514 are adjustable, as will be described momentarily, which allows cross bar assembly 516 to be adjusted along the support rails 502 to achieve a desired spacing relative to cross bar assembly 518. As mentioned previously, cross bar assembly 518 supports 508 and 510, are not moveable along the support rails 502.

Referring now to FIG. 36, the construction of support 510 will be described in greater detail. Initially, cross bar assembly 518 includes a cross bar 528 which is coupled to the end support 524. End support 524 essentially forms a yolk having arms 530 with openings 532 longitudinally aligned and extended therethrough. Arms 530 are disposed over a circumferential boss portion 534 of a mounting element 536. The circumferential boss portion 534 has a bore 538 extending therethrough. A pivot pin 540 extends through the openings 532 and through the bore 538 to pivotally couple the end support 524 to the mounting element 536.

With further reference to FIG. 36, the mounting element 536 includes a stud 542 which projects through an opening 544 in a base portion 546 of the support. 510. At least one fastening element 548 extends through a second opening 550 in the base portion 546 and into a portion of the support rail 502 to fixedly secure the base portion 546 to the support rail 502, such as with a threaded fastener (not shown). The stud 542 of the mounting element 536 extends through the opening 544 in the base portion 546, through a wave washer 552, through a flat washer 554 and is secured to a threaded nut 556. This holds the mounting element 536 securely to the base 546 but allows pivoting of the mounting element 536 about stud 542 to allow cross bar assembly 518 to be rotated from its stowed position to its operative position of FIG. 35.

With further brief reference to FIG. 36, the support rail 502 can also be seen to include a channel insert 558. Channel insert 558 may comprise a roll formed piece of aluminum or metal and is adapted to fit within a recess 560 formed in the support rail 502. Channel insert 558 is fixedly secured to the support rail 502 by plurality of fastening elements 562 secured and spaced along portions of the channel insert 558.

Referring now to FIG. 37, the construction of end support 522 and support assembly 512 will be described. End support 522 is essentially identical in construction to end support 524 and includes arms 564 having openings 567 formed therein. The arms 564 fit over a circumferential boss portion 568 of a mounting element 566 having a bore 570 therethrough. A mounting pin 572 extends through openings 567 and through bore 570 to secure the end support 522 to the mounting element 566 and allow pivotal movement of the cross bar assembly 516 about the mounting element 566. The mounting element 566 also has a stud 574 which projects through a bore 576 in a base 578 of the support 512. The stud 574 is secured to a threaded nut 580 such that a wave washer 582 and a flat washer 584 are captured by the threaded nut 580. The wave washer 582 provides a small degree of tension to prevent rattling of the end support 522 on the base 578, while still allowing pivotal movement of the mounting element 566 about the base 578 when the cross bar assembly 516 is moved from its stowed to its operative position.

An additional advantage of the base 578 is a front portion 584 and the inclusion of an actuating lever 586 permitting the base 578 to be secured at various positions along the support rail 502 so that the cross bar assembly 516 can be adjustably positioned along the support rails 502. The front portion 584 of the base includes a T-lug 588 for resting within a channel insert 590 of the support rail 502. Channel insert 590 forms the channel 506 and, again, may be a roll formed, aluminum component that is secured by a suitable plurality of fasteners within a channel 592 of the support rail 502. The actuating member 586 includes a manually graspable portion 594 and a stud 596. Stud 596 projects through a bore 598 in the front portion 584 of the base 578 and through an opening 600 in a leaf-type biasing spring 602. The biasing spring 602 is adapted to fit within the channel 506 of the channel insert 590 and is secured to the stud 596 via a snap ring 604 or any other like locking element that may be secured to the stud 596. The construction of the actuating member 586 and the means by which it causes a locking action of the leaf-type spring 602 will be described momentarily.

Figure 38:
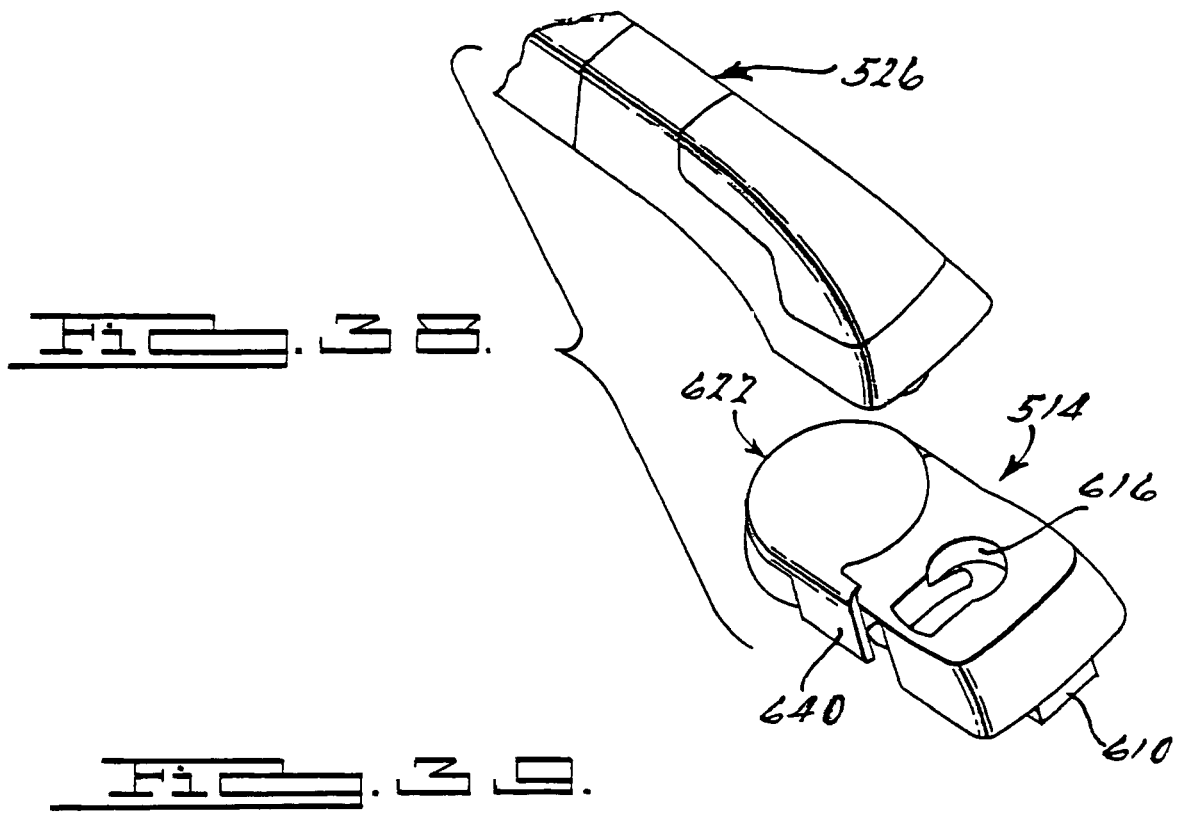
FIG. 38 is a perspective view of one of the longitudinally adjustable mounting assemblies and one end support adapted to be releasably secured thereto.
Figure 39:
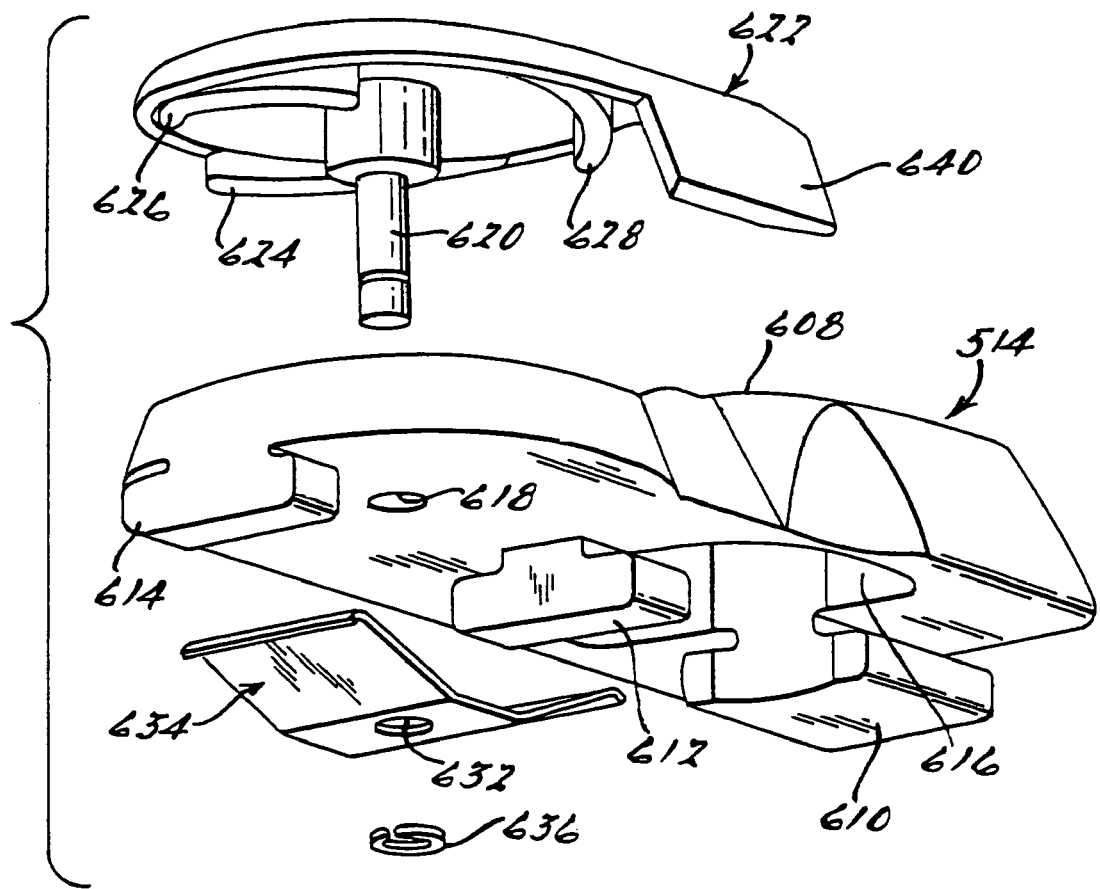
FIG. 39 is a bottom perspective view of the component parts of one of the longitudinally adjustable mounting assemblies of the vehicle article carrier.

Referring now to FIGS. 38 and 39, the construction of end support 526 and support assembly 514 will be described. Turning initially to FIG. 39, support assembly 514 comprises a main body 608 having a plurality of T-lugs 610, 612 and 614 preferably integrally formed with the main body 608. A first opening 616 receives a portion of the end support 526, which will be described momentarily, and an opening 618 receives a stud 620 of an actuating member 622. It will be appreciated that actuating member 622 and actuating member 586 (FIG. 37) are identical in construction.

Referring further to FIG. 39, the actuating member 622 further includes a plurality of camming surfaces 624, 626 and 628 spaced circumferentially from one another. A manually engageable portion 640 allows a user to rotate the actuating member 622. The stud 620 projects through the opening 618 and through a hole 632 in a leaf-type biasing member 634 and is secured with a locking clip 636. Leaf-type biasing member 634 is essentially identical to leaf-type biasing member 602 (FIG. 37) and is adapted to reside within channel insert member 558, which is identical to channel insert member 590 (FIG. 37). T-Lugs 610, 612 and 614 fit within the channel insert member 558 to allow the support assembly 514 to be moved slideably along the channel 506 of the support rail 502 without being removable therefrom.

Figure 40:
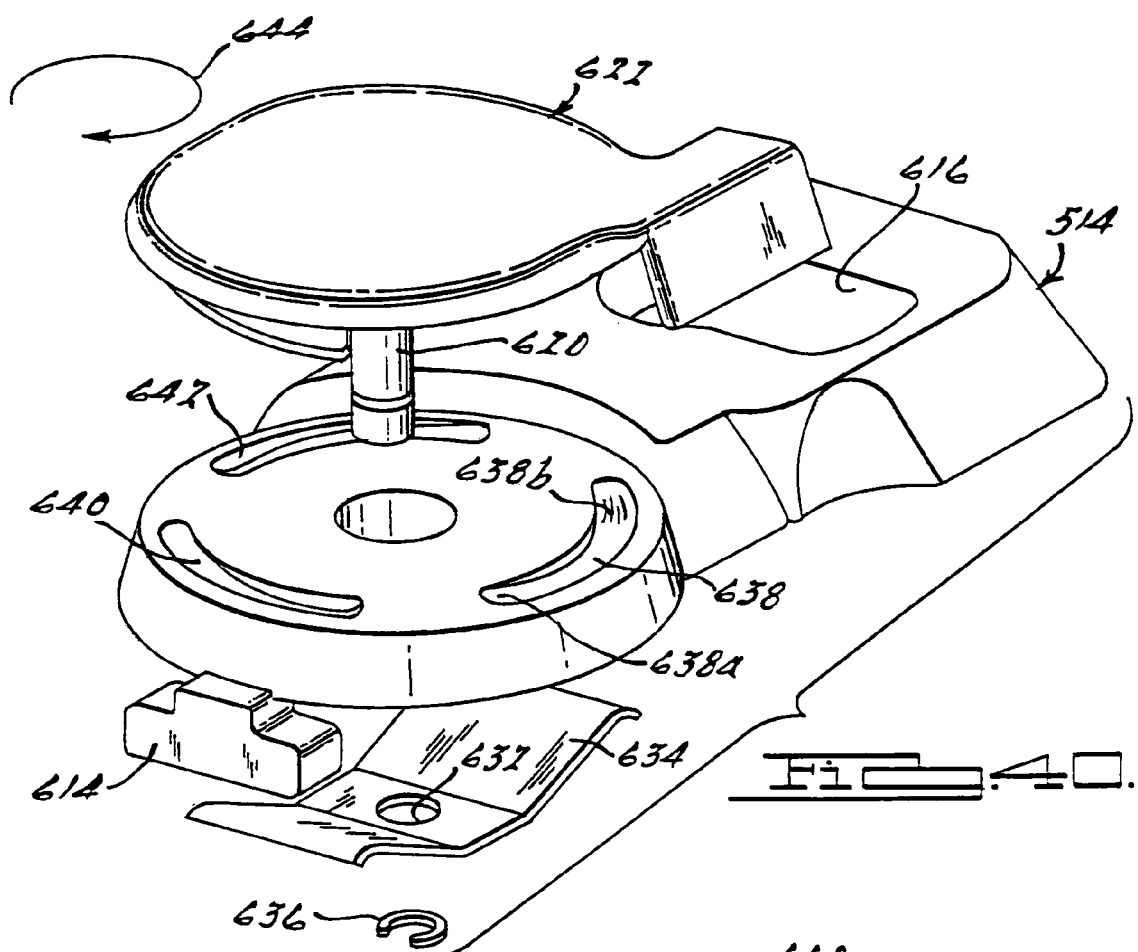
FIG. 40 is an upper perspective view of the mounting assembly of FIG. 39.

With brief reference to FIG. 40, the main body 608 can be seen to include a plurality of circumferential grooves 638, 640 and 642. These grooves 638, 640 and 642 vary in depth from the minimum at one end of each, for example at end 638A of groove 638, to a maximum at end 638B. Accordingly, when the actuating member 622 is assembled to the main body 608 the camming portions 624, 626 and 628 each reside within a respective one of the grooves 638, 640 and 642. As the actuating member 622 is rotated clockwise in the drawing of FIG. 40 (i.e., in accordance with arrow 644), the actuating member 622 is lifted as the camming surfaces 624, 626 and 628 ride in the grooves 638, 640 and 642. This causes the stud 620 to be lifted which tends to flatten the leaf-type biasing member 634 secured thereto. When this occurs, the leaf-type biasing member 634 is no loner frictionally engaged within its associated channel 506, and the support assembly 514 is able to be moved slideably along its associated support rail 502. When the actuating member 622 is in the orientation showing in FIG. 40 and fully assembled to the main body 608, the leaf-type biasing member 634 will essentially be in the shape shown in FIG. 40. The leaf-type biasing member 634 will engage a lower wall surface of the channel insert member 658, thus locking the support assembly 514 at a specific position along its associated support rail 502.

Figure 41:
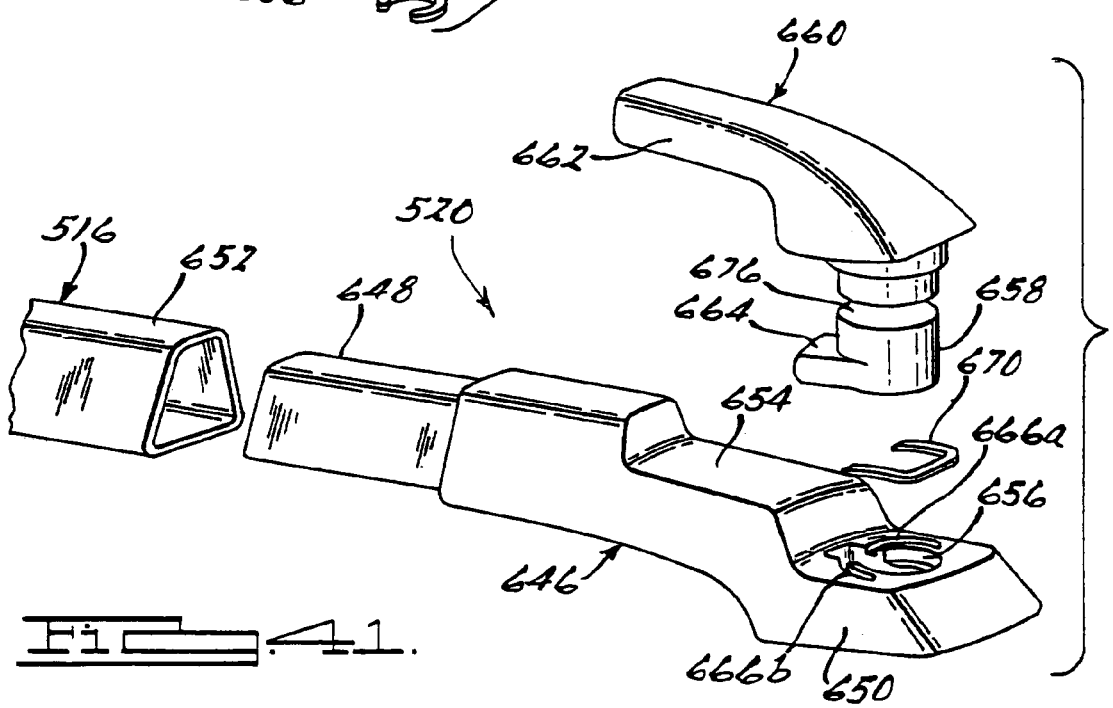
FIG. 41 is an exploded perspective view of one of the end supports.

Referring further to FIG. 38 and FIG. 41, the construction of the end support 520 will be described in greater detail. The end support 520 includes a main body portion 646 having a neck 648 and a mounting portion 650. The neck 648 is shaped so as to be telescopically received within an end of a cross bar member 652 of cross bar assembly 516 and fixedly secured therein via a threaded fastening element or any other suitable fastener. The mounting portion 650 includes a recessed area 654 and an opening 656. Protruding through the opening 656 is a neck 658 of a rotatable locking member 660. The locking member 660 includes a manually graspable portion 662 and an end portion 664. With brief reference to FIGS. 42 and 43, the mounting portion 650 includes a pair of circumferential grooves 666a and 666b formed on opposite sides of the opening 656. The opening 656 also is key-shaped to allow the end portion 664 of the locking member 660 to be inserted through the opening 656 during assembly. With further reference to FIG. 43, a groove 668 is adapted to receive a wave washer 670 therein. The function of the wave washer 670 will be explained momentarily.

Figure 42:
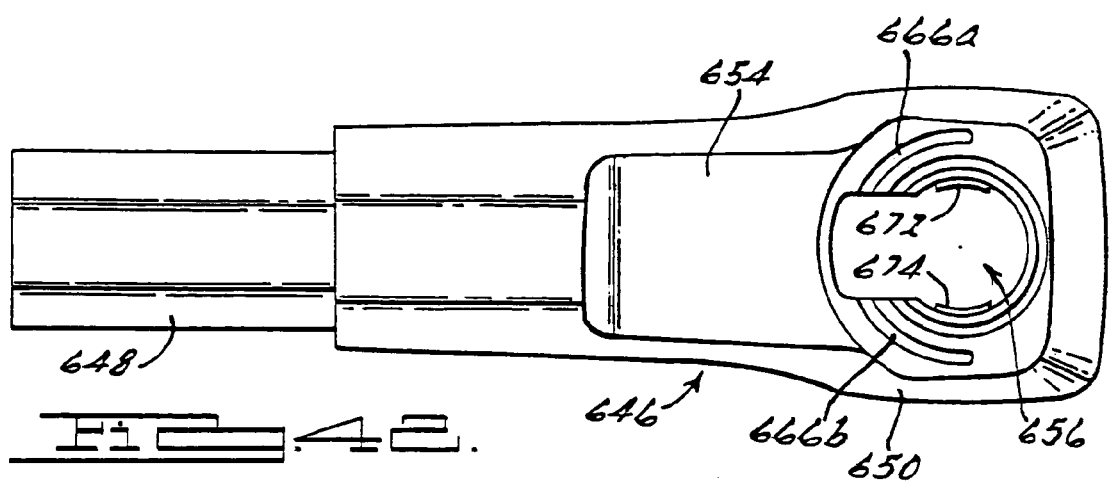
FIG. 42 is a plan view of an upper surface of one of the end supports without the locking member secured thereto.
Figure 43:
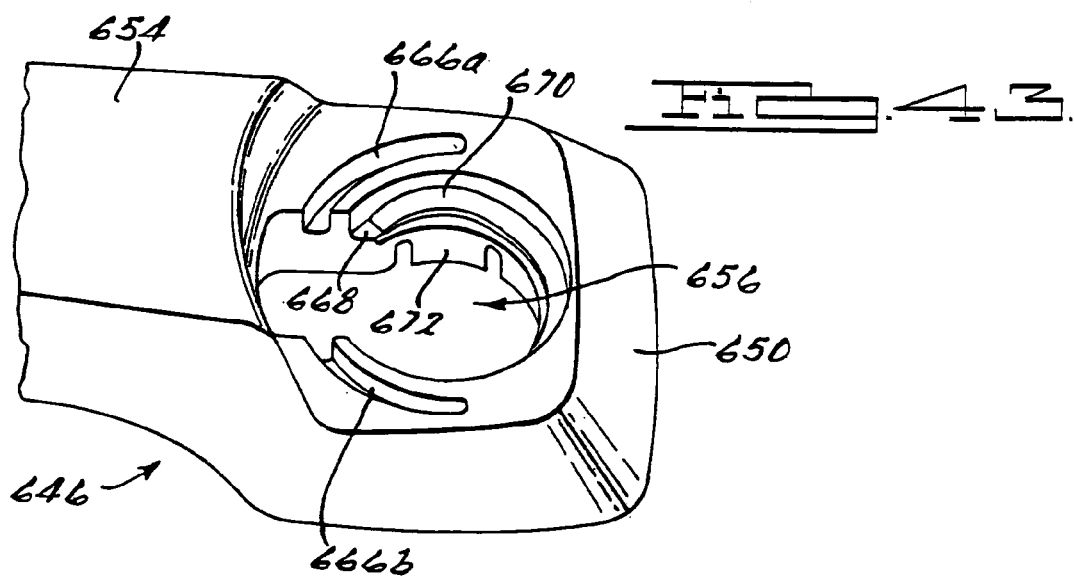
FIG. 43 is a perspective view of a portion of the end support.
Figure 44:
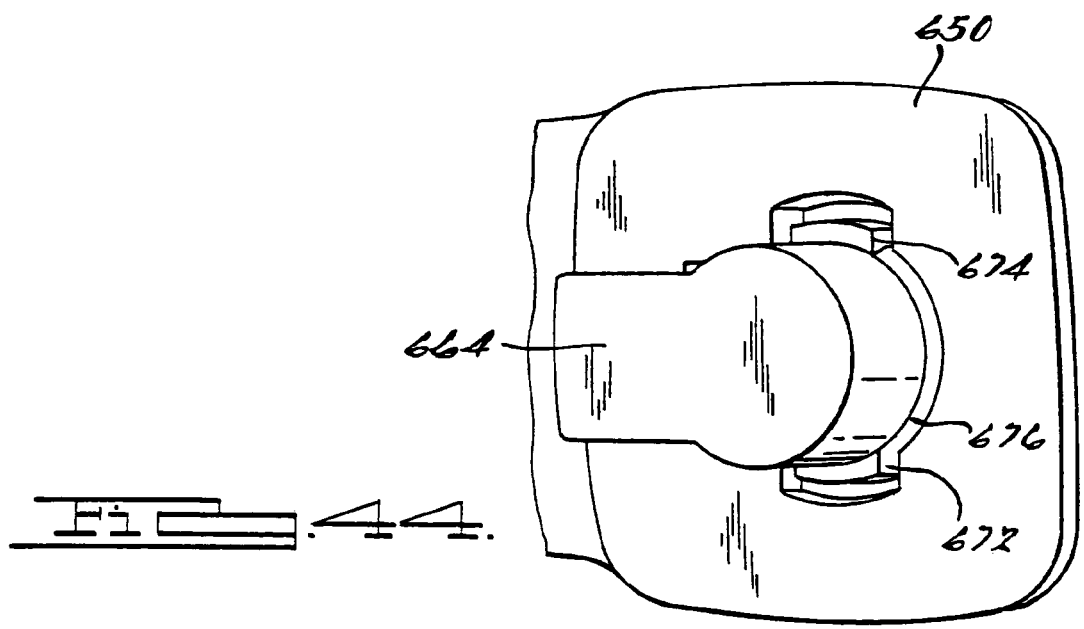
FIG. 44 is a bottom view of a portion of the end support of FIG. 41 showing the engagement of the locking member therewith.
Figure 4S:
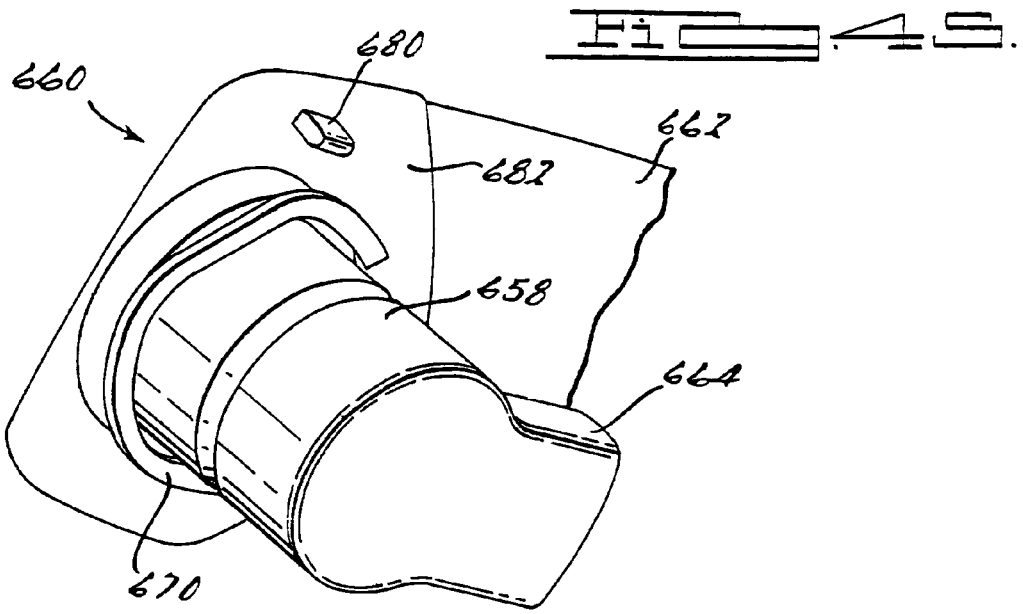
Figure 4B:
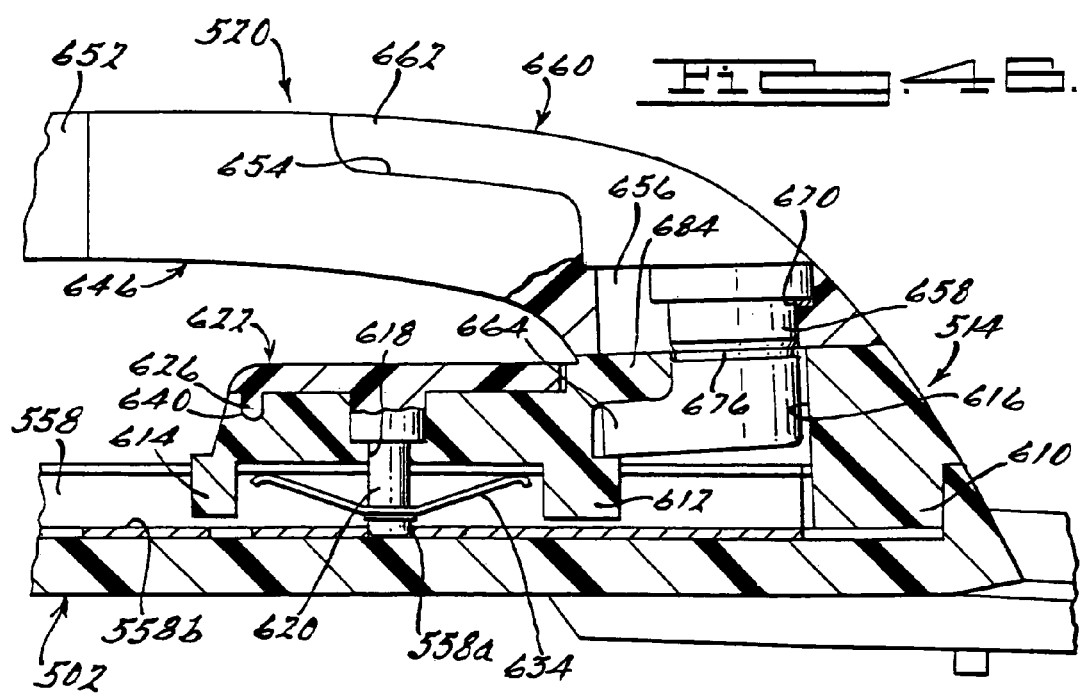

With reference to FIGS. 42-44, the mounting portion 650 further includes a pair of integrally formed catch portions 672 and 674. Catch portions 672 and 674 are slightly resilient and are adapted to engage a groove 676 (FIG. 41) on the neck 658 of the locking member 660. Thus, to assemble the locking member 660 to the mounting portion 650, the neck 658 is inserted through the opening 656 and the catch portions 672 and 674 automatically, snappingly engage the groove 676 when the locking member 660 is fully seated on the mounted portion 650.

With brief reference to FIG. 45, an undersurface of the locking member 660 can be seen. An integrally formed projection 680 protrudes from an undersurface 682 of the locking member 660. The projection 680 is adapted to ride within the grooves 666A and 666B and to limit rotational movement of the locking member 660 when it is moved between its locked and unlocked positions.

Figure 47:
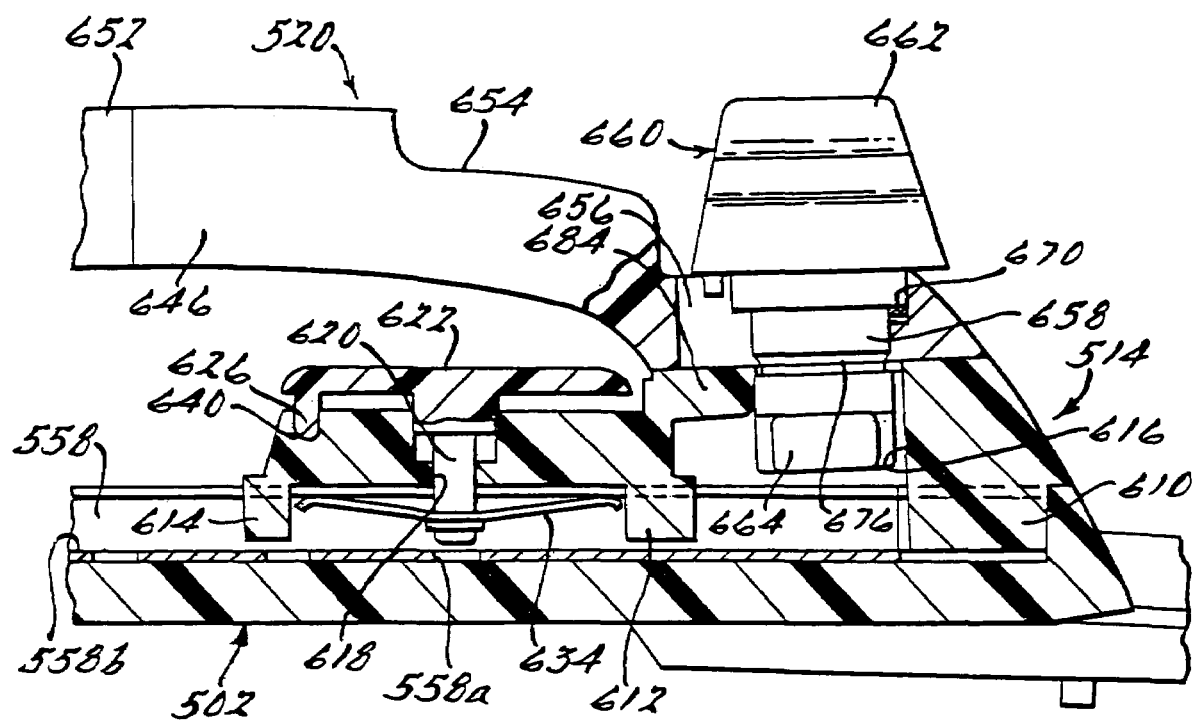
FIG. 47 is a side cross sectional view of the end support of FIG. 44 showing the end support in the unlocked position and the longitudinally adjustable support assembly in an unlocked position.

With brief reference to FIG. 46, the end support 520 is shown attached to the support assembly 514. The end portion 664 abuts a portion 684 of the main body 608. The wave washer 670 is held in a "flattened" condition once the locking member 660 is assembled to the mounting member 514 and thus prevents any rattling of the locking member 660 during operation of the vehicle on which the vehicle article carrier 500 is mounted. The leaf-type biasing member 634 is shown biasing the stud 620 into one hole 558a of a plurality of holes 528a formed in a bottom wall 558b of the channel insert 558. With brief reference to FIG. 47, the locking member 660 has been rotated 90° to place the end portion 664 in an orientation able to be lifted through the key shaped opening 616 in the main body 608 of the support assembly 514. Thus, both the locking member 660 and the actuating member 622 can be moved within generally parallel, horizontal planes to allow removal of the cross bar assembly 516 from the support assembly 514, or to allow repositioning of the support assembly 514 along its associated support rail 502.

It will be appreciated that the construction of end support 526 is identical to end support 520. As such, end support 526 can be readily coupled to support member 508 when cross bar assembly 518 is to be configured in its operative position extending between the two support rails 502.

Figure 48:
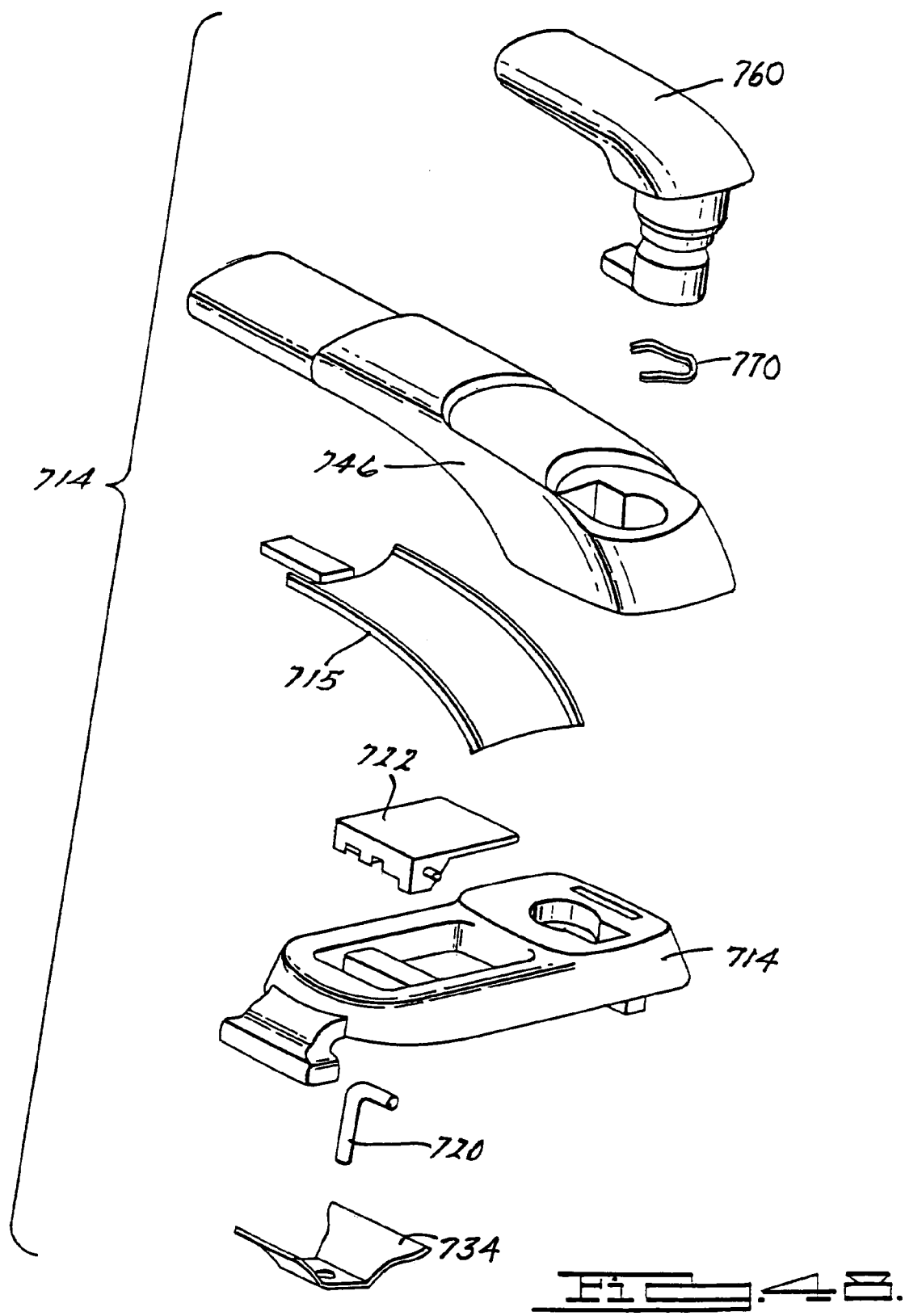
FIG. 48 is an exploded perspective view of the components of one end support in accordance with an alternative preferred embodiment of the present invention.

Referring to FIG. 48, a support assembly 714 in accordance with an alternative preferred embodiment of the support assembly 514 is shown. Components of support assembly 714 that are in common with components of assembly 514 are indicated with reference numbers increased by 100 or 200 over those used in connection with the description of support assembly 514.

Support assembly 714 differs from support assembly 514 only in the use of an upwardly pivoting actuating member 722 and L-shaped stud 720, rather than rotationally moving actuating member 522 and generally linear stud 620. This configuration is disclosed in U.S. Pat. No. 5,826,766, issued Oct. 27, 1998, and assigned to JAC Products, Inc., the disclosure of which is hereby incorporated by reference into the present application. Other suitable locking assemblies that may be incorporated with various degrees of modification to the present invention are disclosed in U.S. Pat. No. 5,833,103, issued Nov. 10, 1998 and U.S. Pat. No. 5,794,827, issued Aug. 18, 1998, both assigned to JAC Products, Inc., and both also being incorporated by reference into the present application. A lower cover member 715 is secured, such as by threaded fasteners (not shown), to the main body portion 746.

Referring now to FIGS. 49 and 50, an article carrier 800 in accordance with an alternative preferred embodiment of the present invention is shown. This embodiment is similar to the vehicle article carrier 500 with the exception that each cross bar assembly 816 is removable at both ends thereof from a pair of support rails 802 or 803 to which the cross bar assemblies 816 can be attached. Support assemblies 814, which are identical to support assemblies 714, are illustrated being secured to support rails 802. However, it will be appreciated that support assemblies in accordance with support assembly 514 could also be employed. The side rails 802 have a plurality of spaced apart openings 802a at which the support assemblies 814 can be positively secured. Preferably a mounting pad 805 or gasket is disposed underneath each side rail 802 or 803 and an outer body surface 807.

Referring to FIG. 50, support rails 803 include base portion 803a, cover 803b, which may be secured to its respective base portion with threaded fasteners (not shown) or by any other suitable means, and a keyed opening 803c identical to opening 616 in support assembly 514 (FIG. 40). Keyed opening 803c enables either end of either cross bar assembly 816 to be secured thereto. In this manner the cross bar assemblies 816 can be secured in the operative position to span between the support rails 802 and 803 (FIG. 50), or in a stowed position (indicated in phantom in FIG. 49) parallel to a respective side rail pair 802/803.

Referring to FIG. 51, an article carrier 900 in accordance with another alternative preferred embodiment of the present invention is shown. Article carrier 900 is similar to article carrier 800, and similar components are designated by reference numerals increased by 100 over those used in connection with article carrier 800. Article carrier is secured to an outer body surface 907 of a vehicle and may or may not include a gasket or pad mounted underneath each article.

Article carrier 900 includes a pair of rear side rails 902 and a pair of front side rails 903, which can each support a cross bar assembly 916. However, with article carrier 900, the cross bar assembly 916 supported on rear side rails 902 is positioned in either one of two distinct positions, rather than along a larger plurality of locations as with the article carrier 800. For purposes of illustration, a pair of cross bar assemblies 916 are shown secured to the rear side rails 902 to illustrate the two operative positions that the rear cross bar assembly 916 can used at. In practice, however, a single cross bar assembly 916 will be used in connection with the rear side rails 902.

Referring to FIG. 52, each of the rear side rails 902 includes a pair of keyed openings 902a identical to that shown in connection with article carrier 800. The keyed opening 902a at a front end 909 of each side rail 902 is used when the cross bar assembly 916 is to be held in its stowed position, with one end of the cross bar assembly 916 secured to its associated rear side rail 902 and the other end secured to its associated front side rail 903. While the rear side rails 902 each include two distinct positions at which an end one of the side rail assemblies 916 can be secured, it will be appreciated that a greater or plurality of distinct positions (each defined by a keyed opening 902a) could be employed. In such instance, the overall length of the side rails 902 may or may not need to be lengthened.

Figure 53:
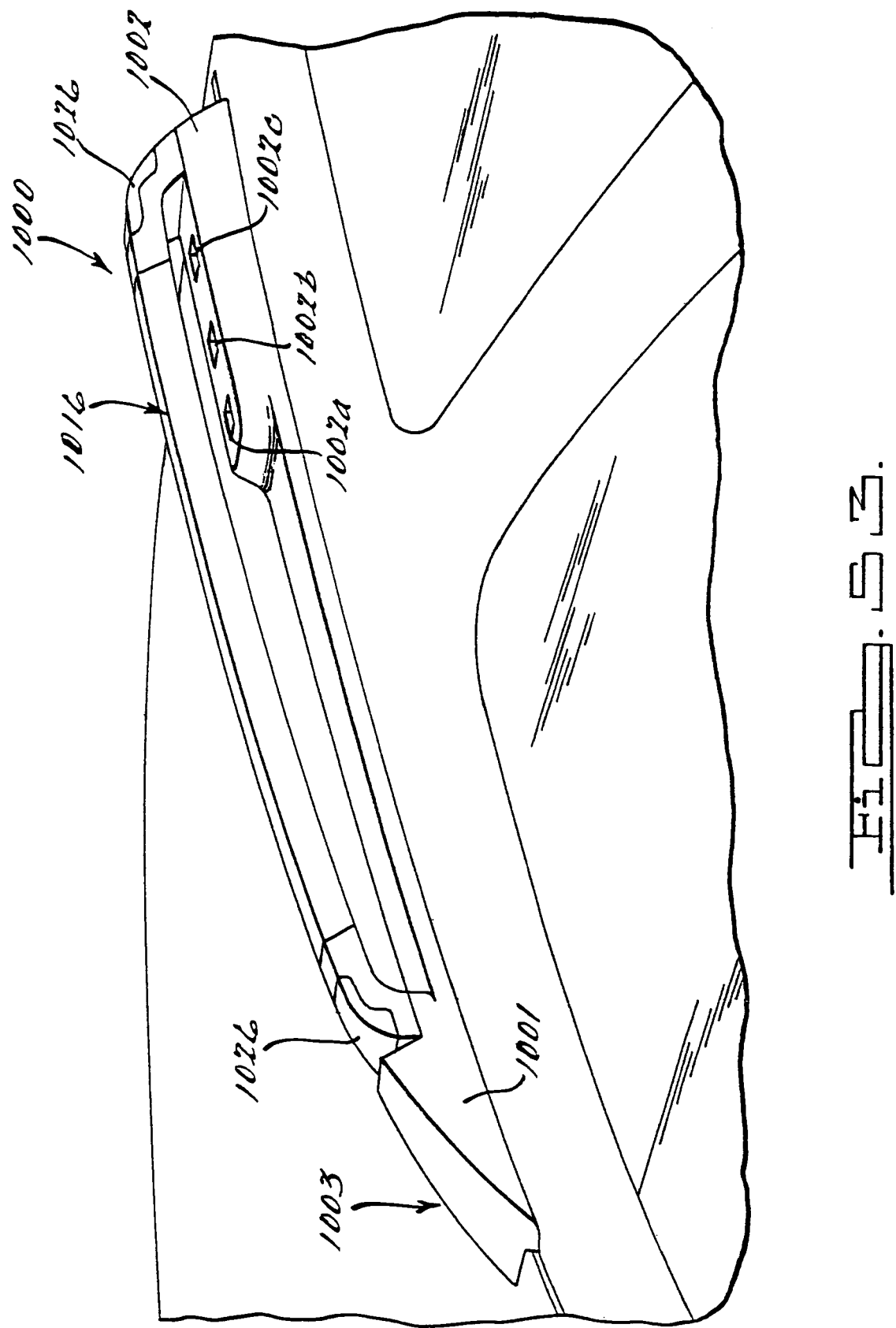
FIG. 53 is a perspective view of yet another alternative preferred embodiment of the vehicle article carrier that includes side rails having a plurality of predetermined mounting locations formed thereon to enable an associated cross bar to be secured at a plurality of longitudinal positions thereon.

Referring to FIG. 53, a side rail assembly 1000 in accordance with an alternative preferred embodiment of article carrier 900 is shown. Side rail assembly 1000 includes a side rail 1001 having a rear portion 1002 and a front portion 1003. A cross bar assembly 1016 is secured to the front portion 1003 and the rear portion 1002 to illustrate the cross bar assembly in its stowed configuration. Rear portion 1002 includes keyed openings 1002a, 1002b and 1002c. The front portion 1003 includes a keyed opening (not shown) for securing the end support 1026 (which is identical in construction to end support 526). Thus, side rail assembly 1000 allows four distinct, operative positions for the cross bar assembly 1016 when the assembly 1016 is positioned to span between a pair of the side rail assemblies 1000.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification, and following claims.

What is claimed is:

1. A vehicle article carrier comprising:
    a first side rail;
    a second side rail spaced apart from said first side rail;
    first and second crossbar mounts moveably coupled to said first side rail;
    third and fourth crossbar mounts moveably coupled to said second side rail;
    a first crossbar pivotally coupled to said first crossbar mount at a first end and removably secured to said second crossbar mount at a second end in a stowed mode, and removably secured to said third crossbar mount at said second end in a spanning mode;
    a second crossbar pivotally coupled to said fourth crossbar mount at one end and removably secured to said third crossbar mount at a second end in a stowed mode, and removably secured to said second crossbar mount at said second end in a spanning mode; and
    wherein each of said cross bar mounts are adjustable to be secureable at an infinite number of points along said side rails.

2. The vehicle article carrier of claim 1, wherein said side rails each comprise elevated side rails adapted to be positioned above an outer body surface of a vehicle on which said article carrier is mounted.

3. The vehicle article carrier of claim 2, wherein said side rails each form a channel, said channels being positioned to open towards one another.

4. The vehicle article carrier of claim 1, wherein each of said cross bar mounts includes a manually engageable wheel and an associated tapped plate disposed within said side rail for securing it at a desired position along said associated side rail.

5. The vehicle article carrier of claim 1, wherein each of said cross bars includes a securing mechanism at one end thereof for releasably securing said one end to one of a designated pair of said cross bar mounts.

6. The vehicle article carrier of claim 1, wherein said securing mechanism includes a manually engageable wheel that is threadably coupled to a portion of one of said cross bar mounts.

7. The vehicle article carrier of claim 1, wherein said first crossbar is pivotally and removably mounted to said first crossbar mount at said one end and said second crossbar is pivotally and removably coupled to said fourth crossbar mount at said one end.

8. The vehicle article carrier of claim 1, wherein said second crossbar mount includes a nub engaging a latch of said first crossbar in said stowed mode and a latch of said second crossbar in said spanning mode, and said third crossbar mount includes a nub engaging a latch of said first crossbar in said spanning mode and a latch of said second crossbar in said stowed mode.

9. A vehicle article carrier apparatus for supporting articles elevationally above an outer body surface of a vehicle, said apparatus comprising:
    a first side rail;
    a second side rail spaced apart from said first side rail;
    a first cross bar being pivotally connected at a first end to a first one of said side rails;
    a second cross bar being pivotally connected at a first end to a second one of said side rails;
    said first cross bar being secureable in a stowed position at a second end thereof to said first side rail, so as to be laying parallel to said first side rail;
    said second cross bar being secureable at a second end to said second side rail so as to be laying parallel to said second side rail;
    said first cross bar being movable pivotally into a spanning position extending between said side rails, and releasably secureable at said second end thereof to said second side rail;
    said second cross bar being movable pivotally into a spanning position extending between said side rails, and releasably secureable at said second end thereof to said first side rail; and
    wherein at least one of said cross bars includes a moveable shroud at said second end to assist in enabling coupling of said one cross bar in said spanning position.

10. The apparatus of claim 9, wherein said moveable shroud is coupled to said one cross bar by a fastening member passing though a slot formed in one of said one crossbar and its associated said shroud.

11. The vehicle apparatus of claim 9, wherein each of said side rails includes a mount assembly secured thereto that can be positioned slidably along its associated said side rail.

12. The apparatus of claim 11, wherein each of said mount assemblies includes a securing mechanism enabling it to be immovably secured at a desired position along its associated said side rail.

13. The apparatus of claim 12, wherein said securing mechanism comprises a manually engageable wheel that can be tightened and loosened with a single hand.

14. The apparatus of claim 13, further comprising separate tapped plates disposed within each of said side rails and operable with an associated one of said mount assemblies to secure said associated mount assembly to said side rail at a desired position along said side rail.

15. The apparatus of claim 11, wherein at least one of said movable shrouds includes a pivotally mounted latch adapted to engage with one of said mount assemblies.

16. The apparatus of claim 15, wherein said at least one of said mount assemblies includes a member projecting therefrom adapted to engage with said latch.

17. The apparatus of claim 10, wherein said movable shroud includes a housing having a recess, said recess housing a pivotally mounted latch adapted to engage with one of said mount assemblies.

18. The apparatus of claim 17, further comprising a biasing member operably associated with said movable shroud for providing a constant biasing force on said latch to hold said latch in a normally latched position.

19. A vehicle article carrier apparatus comprising for supporting articles elevationally above an outer body surface of a vehicle, said apparatus comprising:

a first side rail;
a second side rail spaced apart from said first side rail;
a first cross bar being pivotally connected at a first end to said first side rail;
a second cross bar being pivotally connected at a first end to said second side rail;
said first cross bar being secureable in a stowed position such that a second end thereof is secured to said first side rail, such that said first cross bar lays parallel to said first side rail;
said second cross bar being secureable in a stowed position such that a second end thereof is secured to said second side rail such that said second cross bar lays parallel to said second side rail;
said first cross bar being movable pivotally into a spanning position extending between said first and second side rails, and releasably secureable at said second end thereof to said second side rail;
said second cross bar being movable pivotally into a spanning position extending between said first and second side rails, and releasably secureable at said second end thereof to said first side rail; and
at least first and second movable cross bar mount assemblies secured to said first and second side rails respectively, said cross bar mount assemblies each including a manually engageable securing member for clamping each said cross bar mount assembly at an infinite number of positions along its associated said side rail, each said cross bar mount assembly further including a portion for releasably engaging said second end of either one of said first and second cross bars to facilitate securing of said first and second cross bars in said stowed and spanning positions.

20. A vehicle article carrier comprising:
a first side rail;
a second side rail spaced apart from said first side rail;
first and second crossbar mounts moveably coupled to said first side rail;
third and fourth crossbar mounts moveably coupled to said second side rail
a first crossbar pivotally coupled to said first crossbar mount at a first end and removably secured to said second crossbar mount at a second end in a stowed mode, and removably secured to said third crossbar mount at said second end in a spanning mode;
a second crossbar pivotally coupled to said fourth crossbar mount at one end and removably secured to said third crossbar mount a second end in a stowed mode, and removably secured to said second crossbar mount at said second end in a spanning mode; and
wherein each of said cross bar mounts includes in manually engageable wheel and associated tapped plate disposed within said rail for securing it at a desired position along its associated said side rail.

* * * * *

UNITED STATES PATENT AND TRADEMARK OFFICE
CERTIFICATE OF CORRECTION

PATENT NO. : 7,448,523 B2 Page 1 of 1
APPLICATION NO. : 10/925660
DATED : November 11, 2008
INVENTOR(S) : Jeffrey M. Aftanas et al.

It is certified that error appears in the above-identified patent and that said Letters Patent is hereby corrected as shown below:

Title Page: Item (60), Related U.S. Application Data

Line 7: "10/279,295" should be --10/279,285--

Signed and Sealed this

Thirteenth Day of January, 2009

JON W. DUDAS
*Director of the United States Patent and Trademark Office*